(12) United States Patent
Soerensen et al.

(10) Patent No.: US 9,988,442 B2
(45) Date of Patent: Jun. 5, 2018

(54) MFAP4 BINDING ANTIBODIES BLOCKING THE INTERACTION BETWEEN MFAP4 AND INTEGRIN RECEPTORS

(71) Applicant: SYDDANSK UNIVERSITET, Odense M (DK)

(72) Inventors: Grith Lykke Soerensen, Odense S (DK); Anders Schlosser, Odense M (DK); Uffe Holmskov, Odense S (DK)

(73) Assignee: SYDDANSK UNIVERSITET, Odense M (DK)

( * ) Notice: Subject to any disclaimer, the term of this patent is extended or adjusted under 35 U.S.C. 154(b) by 139 days.

(21) Appl. No.: 14/762,086

(22) PCT Filed: Jan. 22, 2014

(86) PCT No.: PCT/DK2014/050011
§ 371 (c)(1),
(2) Date: Jul. 20, 2015

(87) PCT Pub. No.: WO2014/114298
PCT Pub. Date: Jul. 31, 2014

(65) Prior Publication Data
US 2015/0361165 A1 Dec. 17, 2015

Related U.S. Application Data

(60) Provisional application No. 61/755,484, filed on Jan. 23, 2013.

(30) Foreign Application Priority Data

Jan. 23, 2013 (DK) ................................ 2013 70033

(51) Int. Cl.
| | | |
|---|---|---|
| C07K 16/00 | (2006.01) | |
| C07K 16/28 | (2006.01) | |
| A61K 39/395 | (2006.01) | |
| G01N 33/53 | (2006.01) | |
| C07K 16/18 | (2006.01) | |
| C12N 5/16 | (2006.01) | |

(52) U.S. Cl.
CPC .............. *C07K 16/18* (2013.01); *C07K 16/28* (2013.01); *C12N 5/163* (2013.01); *C07K 2317/56* (2013.01); *C07K 2317/73* (2013.01); *C07K 2317/76* (2013.01)

(58) Field of Classification Search
None
See application file for complete search history.

(56) References Cited

U.S. PATENT DOCUMENTS

| | | |
|---|---|---|
| 6,916,605 B1 | 7/2005 | McCafferty et al. |
| 7,189,841 B2 | 3/2007 | Lerner et al. |
| 7,959,923 B2 | 6/2011 | You et al. |
| 2005/0048057 A1 | 3/2005 | Day et al. |
| 2011/0059097 A1 | 3/2011 | Zhang et al. |
| 2011/0076284 A1 | 3/2011 | Corbin et al. |
| 2012/0039907 A1 | 2/2012 | Armour et al. |

FOREIGN PATENT DOCUMENTS

| | | | |
|---|---|---|---|
| WO | WO-01/62930 A1 | | 8/2001 |
| WO | WO-2005/007674 A2 | | 1/2005 |
| WO | WO-2006/062779 | | 6/2006 |
| WO | WO-2009/042746 A1 | | 4/2009 |
| WO | WO-2009/103157 A1 | | 8/2009 |
| WO | WO-2010/042562 | | 4/2010 |
| WO | WO-2011/038302 | | 3/2011 |
| WO | WO-2012/027745 | | 3/2012 |
| WO | WO2016008498 | * | 1/2016 |

OTHER PUBLICATIONS

Booij et al., Functional annotation of the human retinal pigment epithelium transcriptome. BMC Genomics 2009, 10:164, pp. 1-18.*
Brown et al. Tolerance of single, but not multiple, amino acid replacements in antibody VH CDR 2: a means of minimizing B cell wastage from somatic hypermutation? J. Immuno. May 1996, 3285-91.*
Vajdos et al. Comprehensive functional maps of the antigen-binding site of an anti-ErbB2 antibody obtained with shotgun scanning mutagenesis. J. Mol. Biol. Jul. 5, 2002, 320(2):415-28.*
Abdul-Salam VB, Wharton J, Cupitt J, Berryman M. Edwards RJ, Wilkins MR. Proteomic analysis of lung tissues from patients with pulmonary arterial hypertension. Circulation. 2010;122(20):2058-67. Epub Nov. 3, 2010.
Bader BL, Rayburn H, Crowley D, Hynes RO. Extensive vasculogenesis, angiogenesis and organogenesis precede lethality in mice lacking all alpha v integrins. Cell. 1998;95(4):507-19. Epub Nov. 25, 1998.
Baron JH. Moiseeva EP, de Bono DP, Abrams KR, Gershlick AH. Inhibition of vascular smooth muscle cell adhesion and migration by c7E3 Fab (abcixmab): a possible mechanism for influencing restenosis. Cardiovasc Res. 2000;48(3):464-72. Epub Nov. 25, 2000.
Carter A. Integrins as target: first phase III trial launches, but questions remain. Journal of the National Cancer Institute. 2010:102(10);675-7. Epub May 13, 2010.
Casscelis W. Migration of smooth muscle and endothelial cells. Critical events in restenosis. Circulation. 1992;85(3):723-9. Epub Sep. 1, 1992.
Cho A, Reidy MA. Matrix metalloproteinase-9 is necessary for the regulation of smooth muscle cell replication and migration after arterial injury. Circ Res. 2002;91(9):845-51, Epub Nov. 2, 2002.
Choi ET, Khan MF. Leidenfrost JE, Collins ET, Boc KP, Villa BR, et al. Beta3-integrin mediates smooth muscle cell accumulation in neointima after carotid ligation in mice. Circulation. 2004;109(12):1554-9. Epub Mar. 10, 2004.

(Continued)

*Primary Examiner* — Maher M Haddad
(74) *Attorney, Agent, or Firm* — Woodard, Emhardt, Moriarty, McNett & Henry LLP

(57) ABSTRACT

Microfibrillar-associated protein 4 (MFAP4) binding antibodies are provided to prevent or to inhibit the proliferation of vascular smooth muscle cells and neointima formation in blood vessels. Furthermore, there are provided antibodies that effectively inhibit remodelling of vessels and prevent progression of arteriosclerosis as well as restenosis of vessels. The provided antibodies block the interaction between MF AP4 and integrin receptors.

8 Claims, 10 Drawing Sheets

(56) References Cited

OTHER PUBLICATIONS

Corjay MH, Diamond SM, Schlingmann KL, Gibbs SK, Stoltenborg JK, Racanelli AL, alphavbeta3, alphavbeta5, and osteopontin are coordinately upregulated at early points in a rabbit model of neointima formation. Journal of cellular biochemistry. 1999;75(3):492-504. Epub Oct. 28, 1999.
Dufourcq P, Louis H, Moresu C, Daret D, Boisseau MR, Lamaziere JM, et al. Vitronectin expression and interaction with receptors in smooth muscle cells from human atheromatous plaque. Arterioscler Thromb Vasc Biol. 1998;18(2);168-76. Epub Mar. 4, 1998.
Fernandez-Sanchez et al.: Mouse monoclonal antibodies to pneumococcal C-polysaccharide backbone show restricted usage of VH-DH-JH gene segments and share the same kappa chain01D, Immunol. Lett., vol. 123, No. 2, 2009, pp. 125-131.
Fitzpatrick LA, Severson A, Edwards WD, Ingram RT. Diffuse calcification in human coronary arteries. Association of osteopontin with atherosclerosis The Journal of clinical investigation. 1994;94(4):1597-604. Epub Oct. 1, 1994.
Frangogiannis NG. Matricellular proteins in cardiac adaptation and disease. Physiol Rev. 2012;92(2):635-88. Epub Apr. 27, 2012.
Gomez D, Owens GK. Smooth muscle cell phenotypic switching in atherosclerosis. Cardiovasc Res. 2012. Epub Mar. 13, 2012.
Han et al.: Article not published Genbank accession No. ABC86091. 1, Feb. 2, 2006.
Han J et al., Class switch recombination and somatic hypermutation in early mouse B cells are mediated by B cell- and Toll-like receptors. NIH-Public Access Author Manuscript. Jul. 1, 2008. 22 pages.
Han M, Wen JK, Zheng B, Liu Z, Chen Y. Blockade of integrin beta3-FAK signaling pathway activated by osteopontin inhibits neointimal formation after ballon injury. Cardiovascular pathology : the official journal of the Society for Cardiovascular Pathology. 2007:15(5)283-90. Epub Sep. 18, 2007.
Hersey P, Sosman J, O'Day S, Richards J, Bedikian, A, Gonzalez R, et al. A randomized phase 2 study of etaracizumab, a monoclonal antibody against integrin alpha(v)beta(3), or -dacarbazine in patients with stage IV metastatic melanoma. Cancer. 2010:116(6):1526-34. Epub Jan. 29, 2010.
Hirano E. Fujimoto N, Tajima S, Akiyama M, Ishibashi A, Kobayashi R, et al. Expression of 36-kDa microfibril-associated glycoprotein (MAGP-36) in human keratinocytes and its localization in skin. Journal of dermatological science. 2002;28(1).60-7. Epub Mar. 28, 2002.
Hodivala-Dilke KM, McHugh KP, Tsakiris DA, Rayburn H, Crowley D, Ullman-Cullere, M, et al. Beta3-integrin-deficient mice are a model for Glanzmann thrombesthenia showing placental defects and reduced survival. The Journal of clinical investigation. 1999,103(2)229-38. Epub Jan. 23, 1999.
Hoshiga M, Alpers CE, Smith LL, Giachelli CM, Schwartz SM. Alpha-v-beta-3 inetgrin expression in normal and atherosclerotic artery. Circ Res. 1995;77(6):1129-35, Epub Dec. 1, 1995.
Ishigaki T, Imanaka-Yoshida K, Shimojo N, Matsushima S, Taki W, Yoshida T. Tenascin-C enhances crosstalk signaling of integrin alphavbeta3/PDGFR-beta complex by SRC recruitment promoting PDGF-induced proliferation and migration in smooth muscle cells. Journal of cellular physiology. J Cell Physiol. Oct. 2011;226(10):2617-24.
Johnson C, Galis ZS. Matrix metalloproteinase-2 and -9 diffentially regulate smooth muscle cell migration and cell-mediated collagen organization. Arterioscler Thromb Vasc Biol 2004;24(1):54-60. Epub Oct. 11, 2003.
Kasamatsu S, Hachiya A, Fujimura T, Sriwiyanont P, Haketa K, Visscher MO, et al. Essential role of microfibrillar-associated protein 4 in human cutaneous homeostasis in its photoprotection. Scientific Reports. 2011;1(164):1-10.
Kobayashi R, Mizutani A, Hidaka H. Isolation and characterization of a 36-kDa microfibril-associated glycoprotein by the newly synthesized isoquinolinesulfonamide affinity chromatography. Biochem Biophys Res Commun. 1994;198(3):1262-6. Epub Feb. 15, 1994.
Kobayashi R, Tashima Y, Masuda H, Shozawa T, Numata Y, Miyauchi K, et al. Isolation and characterization of a new 36-kDa microfibril-associated glycoprotein from porcine aorta. The Journal of biological chemistry. 1989;264(29):17437-44. Epub Oct. 15, 1989.
Kumar A, Lindner V. Remodeling with neointima formation in the mouse carotid artery after cessation of blood flow. Arteriosler Thromb Vasc Biol. 1997:17(10):2238-44 Epub Nov. 14, 1997.
Li G, Jin R, Norris RA, Zhang L, Yu S, Wu F, et al. Periostin mediates vascular smooth muscle cell migration through the integrins alphavbeta3 and alphavbeta5 and focal adhesion kinase (FAK) pathway. Atherosclerosis. 2010;208(2):358-65. Epub Aug. 22, 2009.
Liaw L, Skinner MP, Raines EW, Ross R, Cheresh DA, Schwartz SM, et al. The adhesive and migratory effects of osteopontin are mediated via distinct cell surface integrins. Role of alpha v beta 3 in smooth muscle cell migration to osteopontin in vitro. The Journal of clinical investigation. 1995;95(2):713-24.
Libby P, Tanaka H. The molecular bases of restenosis. Progress in cardiovascular diseases. 1997;40(2):97-106. Epub Nov. 5, 1997.
Malle LA, Allen LB, Hanzaker CF, Gollahon KA, Dunbar P, Clemmons DR. Glucose regulation of thrombospondin and its role in the modulation of smooth muscle cell proliferation. Experimental diabetes research. 2010;2010. Epub Aug. 7, 2010.
Martin PL, Jiao Q, Cornacoff J, Hall W, Saville B, Nemeth JA, et al. Absence of adverse effects in cynomolgus macaques treated with CNTO 95, a fully human anti-alphav integrin monoclonal antibody, despite widespread tissue binding. Clin Cancer Res. 2005;11(19 Pt 1):6959-65. Epub Oct. 6, 2005.
Mintz GS, Popma JJ, Pichard AD, Kent KM, Satler LF, Wong C, et al. Arterial remodeling after coronary angioplasty: a serial intravascular ultrasound study. Circulation. 1996;94(1):35-43. Epub Jul. 1, 1996.
Molleken C, Sitek B, Henkel C, Poschmann G, Sipos B, Wiese S, et al. Detection of novel biomarkers of liver cirrhosis by proteomic analysis. Hepatology. 2009;49(4):1257-1266. Epub Jan. 30, 2009.
Murphy MG, Cerchio K, Stoch SA, Gottesdiener K, Wu M, Recker R. Effect of L-0008452704, an alphaVbeta3 integrin antagonist on markers of bone turnover and bone mineral density in postmenopausal osteoporotic women. The Journal of clincal endocrinology and metabolism. 2005, pp. 2022-2028. Epub Feb. 3, 2005.
Myers DL, Harmon KJ, Lindner V, Liaw L. Alterations of arterial physiology in osteopontin-null mice. Arterioscler Thromb Vasc Biol. 2003;23(6):1021-8. Epub Apr. 26, 2003.
Nakamura T, Lozano PR, Ikeda Y, Iwanaga Y, Hinek A, Minamisawa S, et al. Fibuiin-5/DANCE is essential for elastogenesis in vivo. Nature. 2002;415(6868):171-5. Epub Jan. 24, 2002.
Owens GK, Kumar MS, Wamhoff BR. Molecular regulation of vascular smooth muscle cell differentiation in development and disease. Physiol Rev. 2004;84(3):767-801. Epub Jul. 23, 2004.
Panda D, Kundu GC, Lee BI, Peri A, Fohl D, Chackalaparampil I, et al. Potential roles of osteopontin and alphaVbeta3 integrin in the development of coronary artery restenosis after angioplasty. Proceedings of the National Academy of Sciences of the United States of America. Aug. 19, 1997;94(17) :9308-13, Epub Aug. 1997.
Peng L, Bhatia, N, Parker AC, Zhu Y, Fay WP. Endogenous vitronectin and plasminogen activator inhibitor-1 promote neointima formation in murine carotid arteries. Arterioscler Thromb Vasc Biol. 2002;22(6):934-9. Epub Jun. 18, 2002.
Pilecki et al.: "Deficiency of microfibrillar-associated protein 4 alleviates allergic inflammation in murine acute model of asthma", Scandinavian Journal of Immunology, vol. 77, No. 4, 2013, pp. 311-312.
Preissner KT, Reuning U. Vitronectin in vascular context: facets of a multitalented matricellular protein. Seminars in thrombosis and hemostasis. 2011;37(4):408-24. Aug. 2, 2011.
Rosenthal MA, Davidson P, Rolland F, Campone M, Xue L, Han TH, et al. Evaluation of the safety, phamacokinetics and treatments effects of an alpha(nu)beta(3) integrin inhibitor on bone turnover

(56) References Cited

OTHER PUBLICATIONS and disease activity in men with hormone-refractory prostate cancer and bone metastases. Asia Pac J Clin Oncol. Mar. 2010; 6(1):42-8.
Ross R. Cell biology of atherosclerosis. Annu Rev Physiol. 1995;57:791-804. Epub Jan. 1, 1995.
Saekmose SG, Schlosser A, Holst R, Johansson SL, Wulf-Johansson H, et al. (2013) Enzyme-linked immunosorbent assay characterization of Basal variation and heritability of systemic microfibrillar-associated protein 4. PLoS One 8: e82383.
Sage EH. Regulation of interactions between cells and extracellular matrix: a command performace on several stages. The Journal of clincal investigation. 2001;107(7):781-3, Epub Apr. 4, 2001.
Sajid M, Stouffer GA. The role of alpha(v)beta3 integrins in vascular healing. Thrombosis and haemostasis. 2002;87(2):187-93. Epub Feb. 23, 2002.
Schlosser A (2004) Microfibril-associated protein 4 (MFAP4) and FReD-1. Two members of the fibrinogen domain superfamily. PHD Thesis: 1-64.
Schlosser A, Thomsen T, Moeller JB, Nielsen O, Tornoe I, Mollenhauer J, et al. Characterization of FIBCD1 as an acetyl group-binding receptor that binds chitin. J Immunol 2009; 183(6):3800-9. Epub Aug. 28, 2009.
Srivatsa SS, Fitzpatrick LA, Tsao, PW, Reilly TM, Holmes DR, Jr., Schwartz RS, et al. Selective alpha v beta 3 integrin blockade potently limits neointimal hyperplasia and lumen stenosis following deep coronary arterial stent injury: evidence for the functional importance of integrin alpha v beta 3 and osteopontin expression during neointima formation. Cardiovasc Research Dec. 1997; 36(3): 408-28.
Thomas AC, Newby AC. Effect of matrix metalloproteinase-9 knockout on vein graft remodelling in mice. J Vasc Res. 2010;47(3):299-308. Epub Dec. 18, 2009.
Thomsen T, Schlosser A, Holmskov U, Sorensen GL. Ficolins and FIBCD1: Soluble and membrane bound pattern recognition molecules with acetyl group selectivity. Molecular Immunology. 2010. Epub Nov. 13, 2010.
Toyoshima T, Ishida T, Nishi N, Kobayashi R, Nakamura T, Itano T. Differential gene expression of 36-kDa microfibril-associated glycoprotein (MAGP)-36/MFAP4) in rat organs. Cell Tissue Res. 2008;332(2):271-278. Epub Mar. 7, 2008.
Toyoshima T, Nishi N, Kusama H, Kobayashi R, Itano T. 36-kDa microfibril-associated glycoprotein (MAG-36) is an elastin-binding protein increased in chick aortae during development and growth. Exp Cell Res. 2005;307(1):224-30, Epub Jun. 1, 2005.
Toyoshima T, Yamashita K, Furuichi H, Shisibori T, Itano T, Kobayashi R. Ultrastructural distribution of 36-kD microfibril-associated glycoprotein (MAGP-36) in human and bovine tissues. J Histochem Cytochem. 1999;47(8):1049-56. Epub Jun. 29, 1999.
van der Flier A, Sonnenberg A. Function and interactions of integrins. Cell Tissue Res. 2001;305(3):285-98. Epub Sep. 27, 2001.
Veradarajulu J, Laser M, Hupp M, Wu R, Hauck CR. Targeting of alpha(v) inetrins interferes with FAK activation and smooth muscle cell migration and invasion. Biochem Biophys Res Commun. 2005;331(2):404-12. Epub Apr. 27, 2005.
Wulf-Johansson H, Lock Johansson S, Schlosser A, Trommelholt Holm A, Melhoit Rasmssen L, et al. (2013) Localization of Microfibillar-Associated Protein 4 (MFAP4) in Human Tissues: Clinical Evaluation of Serum MFAP4 and Its Association with Various Cardiovascular Conditions. PLoS One 8: e82243.
Zhang D, Pier T, McNeel DG, Wilding G, Friedl A. Effects of a monoclonal anti-alphavbeta3 integrin antibody on blood vessels—a pharmacodynamic study. Investigational new drugs. 2007;25(1):49-55, Epub Sep. 27, 2006.
Abstracts—39th meeting of Scandinavian Society for Immunology jointly with the Baltic immunological Society Jun. 2-5, 2010, Tallinn, Estonia.
Kalinina et al.: "Alternative mechanisms of receptor editing in autoreactive B cells", Proc. Natl. Acad. Sci. U.S.A., vol. 108, No. 17, 2011, pp. 7125-7130.
Kokubo T, Uchida H, Choi ET. Integrin alpha(v)beta(3) as a target in the prevention of neointimal hyperplasia. J Vasc Surg. 2007;45 Suppl A; 33-38. Epub Aug. 8, 2007.
Lausen M, Lynch N, Schlosser A, Tomoe I, Saekmose SG, Teisner B, et al. Microfibril-associated protein 4 is present in lung washings and binds to the collagen region of lung surfactant protein D. The Journal of biological chemistry. 1999;274(45):32234-32240.
Perkins C, Yanase N, Smulian G, Gildea L, Orekov T, et al. (2011) Selective stimulation of IL-4 receptor on smooth muscle induces airway hyperresponsiveness in mice. J Exp Med 208: 853-867.
Schlosser A, Thomsen T, Shipley JM, Hein PW, Brasch F, Tornoe I, et al. Microfibril-associated protein 4 binds to surfactant protein A (SP-A) and colocalizes with SP-A in the extracellular matrix of the lung. Scandinavian journal of immunology. 2006;64(2):104-116. Epub Jul. 27, 2006.
Vassilev et al.: "Inhibition of Cell Adhesion by Antibodies to Arg-Gly-Asp (RGD) in Normal Immunoglobulin for Therapeutic Use (Intravenous Immunoglobulin, IVIg)", Blood, vol. 93, 1999, pp. 3624-3631.
Zhao Z, Lee CC, Jiralerspong S, Juyal RC, Lu F, Baldini A, et al. The gene for a human microfibril-associated glycoprotein is commonly deleted in Smith-Magenis syndrome patients. Hum Mol Genet. 1995;4(4):589-97. Epub Apr. 1, 1995.

\* cited by examiner

Figue 2

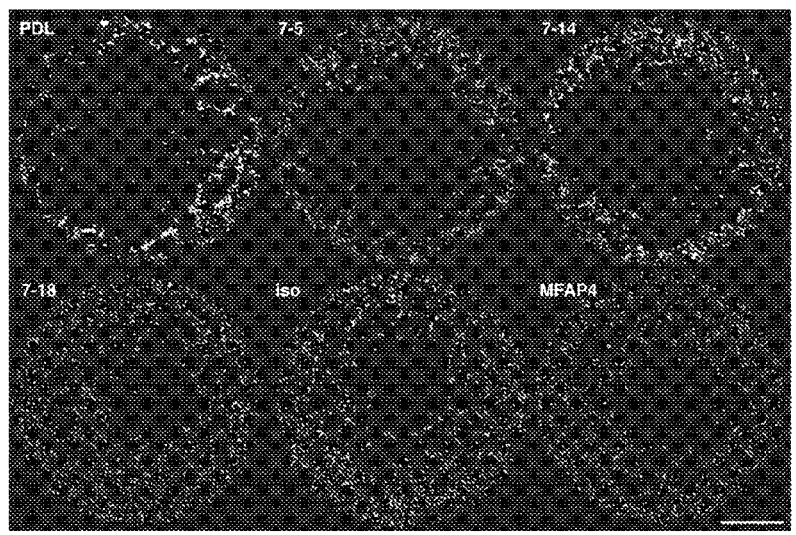
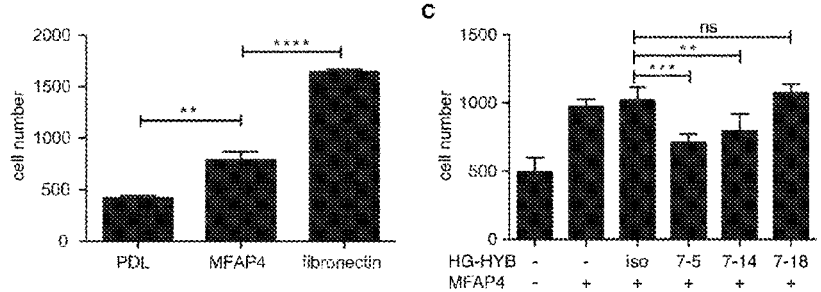
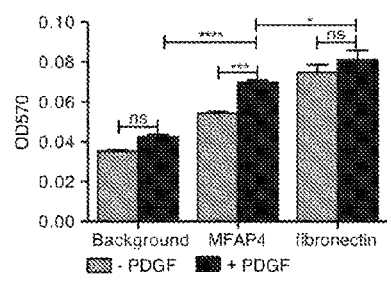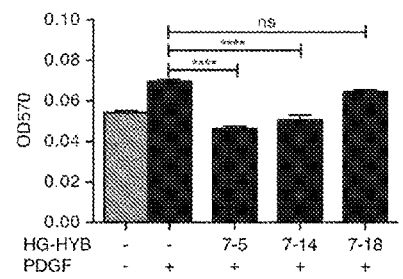
Figure 4

MFAP4 BINDING ANTIBODIES BLOCKING THE INTERACTION BETWEEN MFAP4 AND INTEGRIN RECEPTORS

CROSS REFERENCE TO RELATED APPLICATIONS

The present application is a U.S. National Stage of International Application No. PCT/DK2014/050011 filed on Jan. 22, 2014, which claims the benefit of and priority to Danish Patent Application No. PA 2013 70033 filed on Jan. 23, 2013 and U.S. Provisional Patent Application No. 61/755,484 filed on Jan. 23, 2013, the entire disclosures of all of which are incorporated herein by reference.

FIELD OF THE INVENTION

The invention relates generally to medicine and the use of antibodies. The present invention specifically relates to antibodies, in particular monoclonal, that bind human Microfibrillar-associated protein 4 (MFAP4).

BACKGROUND OF THE INVENTION

Vascular smooth muscle cell activation (VSMC) and phenotypical switch is critical to remodeling processes in vasculoproliferative disorders such as vein graft intimal hyperplasia, restenosis after endovascular interventions, cardiac transplant arteriopathy, pulmonary hypertension and additional obstructive diseases atherosclerosis and restenosis after percutaneus coronary intervention operations (1-5). The initiating events in the cellular activation are triggered by pertubations of the vessel wall and migratory and proliferative activity of VSMCs are key events in the pathologies and the interplay between the extracellular matrix (ECM) and integrins are essential in the control of hyperplasia. Outward remodeling processes may partly reduce the lumen loss, and are involving matrix breakdown by matrix metalloproteinases (MMPs) and result in increments of matrix breakdown products in the circulation.

MFAP4 is a 36 kDa glycoprotein composed of a short N-terminal region that contains a potential integrin binding RGD motiv followed by a fibrinogen related domain (FReD). The protein forms a homo-oligomeric structure under native conditions (6-8). FReDs are found in a diverse group of human proteins involved in different functions such as coagulation, angiogenesis, tissue growth and remodelling, and innate immunity (9).

Studies of MFAP4 or the bovine homologue MAGP-36 has been undertaken since 1989 (10). MAGP-36/MFAP4 was first identified as a protein with tenascin resemblance in the amino acid composition and localized to ECM in arteries (7, 11-14). MAGP-36 was following demonstrated with direct interaction with ECM fibers including elastin, collagen, or calvasculin (11-13, 15). The interaction between MAGP-36 and cellular integrin receptors was demonstrated using inhibition by RGD containing peptides of human aortic smooth muscle cells in attachment to immobilized MAGP-36 (12). All RGD dependent integrins may potentially interact with this RGD site, however integrins $\alpha_V\beta_{3/5}$ are highly relevant for investigation of vascular remodeling. Integrins $\alpha_V\beta_{3/5}$, are known to induce VSMC responses both in vivo and in vitro (16, 17) and may be upregulated during restenosis (18-25). The integrin $\alpha_V\beta_{3/5}$-dimer is expressed in the media in normal arteries (26), yet highly upregulated very early after injury (27, 28).

MFAP4 may be categorized as a matricellular protein due to the localization to matrix fibrils and interactions with smooth muscle cells. Other members of the matricellular family include e.g. tenascin-C; TSP-2 and -4, tenascin-X, and integrin $\alpha_V\beta_{3/5}$ ligands osteopontin, vitronectin, and periostin. Characteristically for such molecules, is that they are not essential for tissue homeostasis, whereas loss of the proteins is associated with a wide range of alterations in the remodeling tissues (29-31).

Besides the localization of MFAP4 in the vessels a soluble form of MFAP4 is present in broncho-alveolar-lavage and in serum (7, 32). Recent proteomic studies have shown MFAP4 to be upregulated in both liver fibrosis (32) and in lung tissue from patients with pulmonary arterial hypertension (33) suggesting that the expression or the turnover of the protein may reflect remodelling processes in diverse tissues.

Detailed mechanisms of progression of arteriosclerosis from pathogenesis to advanced disease are not sufficiently clarified. In addition, detailed mechanisms of vascular remodeling are also unknown. Although there are some reports describing relationships between angiotensin II receptor antagonists and vascular remodeling the effects of calcium channel blockers on pathological changes in arteriosclerosis and vascular damage as well as their mechanisms are little known. Furthermore, since percutaneous coronary intervention (PCI) including percutaneous transluminal coronary angioplasty (PTCA) and stent implantation have low invasiveness, they occupy the central position in current therapeutic strategies against ischemic heart diseases. However, restenosis appearing within several months after surgery in 30-45% patients undergoing these surgical procedures is a major problem. As for the mechanisms of restenosis following PCI, decreases in the diameters of whole vessels in the late period after PCI (that is, remodeling) are considered important, in addition to hyperplasia and hypertrophy of neointima caused by proliferation of smooth muscle cells and accumulation of extracellular matrix, which is produced by the smooth muscle cells. Under these circumstances, development of new medicaments that can effectively prevent restenosis of vessels following PCI is needed. Nevertheless, no medicaments with high efficacy have so far been developed.

Zhao et al (56) discloses human microfibril-associated protein 4 (MFAP4). Zhao et al further discloses that the N-terminus of the protein bears an Arg-Gly-Asp (RGD) sequence that serves as the ligand motif for the cell surface receptor integrin.

VASSILEV T. L. et al. (57) discloses antibodies against ligands to integrins, where the antibodies are against the RGD sequence, resulting in lack of ligand activation of the integrins KOKUBO T. et al. (58) discloses that the blockade of the integrin $\alpha v\beta 3$ by antagonists being either a blocking antibody to $\alpha v\beta 3$ or a $\alpha v\beta 3$-blocking RGD peptide reduced neointima by 70%. KOKUBO T. et al mentions vitronectin, fibronectin, osteopontin, fibrinogen and von Willebrand factor as ligands to $\alpha v\beta 3$ Meanwhile, these prior art documents do not identify a specific receptor for the integrin MFAP4 or antibodies directed to MFAP4 thereby inhibiting the known functions of the integrin receptor. Based on the prior art it could not be predicted that MFAP4 had an effect.

SUMMARY OF THE INVENTION

The subject of the present invention is to provide medicaments, in particular antibodies, for the prevention (the terms "prevention" or "prophylaxis" as used herein include the delaying of the onset of a disease or condition) and/or treatment of cardiovascular proliferative diseases. More concretely, it is the subject of the present invention to provide medicaments, in particular antibodies, to prevent or to inhibit the proliferation or migration of vascular smooth muscles and neointima formation in blood vessels. An additional subject of the present invention is to provide medicaments, in particular antibodies, to prevent or to inhibit inflammatory infiltration and airway remodeling in allergic asthma. Also the prevention or treatment of vascular eye disorders, such as AMD and DR, are contemplated by the inventors.

Based on MFAP4's integrin binding properties and its predominant expression in arteries the present inventors have undertaken the analysis of the role of MFAP4 in arterial remodelling. The inventors have surprisingly found that MFAP4 is synthesized by vascular smooth muscle cells and is a positive regulator of the cellular growth and migration dependent on integrin alphaV-beta3/5 ligation. By construction of mfap4−/− mice and following analysis of these mice in an artery ligation model the inventors observed that activation, proliferation and migration of medial smooth muscle cell were delayed and dysregulated and outward remodelling of the vessel was blunted.

In one aspect of the present invention these antibodies are used to block the interaction between MFAP4 and integrin receptors in order to treat, curatively or preventively, cardiovascular proliferative diseases, such as vein graft intimal hyperplasia, restenosis after endovascular interventions, cardiac transplant arteriopathy, pulmonary hypertension and additional obstructive diseases atherosclerosis and restenosis after percutaneus coronary intervention operations.

In another aspect of the present invention these antibodies are used to block the interaction between MFAP4 and integrin receptors in order to treat, curatively or preventively, allergic asthma.

Specifically the present invention provides an antibody, which specifically blocks the integrin interacting motif in MFAP4 of human MFAP4. Preferably the antibody is selected from isolated polyclonal antiserum, a preparation of purified polyclonal antibodies, or a preparation containing one or more monoclonal antibodies.

Preferred antibodies of the present invention may have the following amino-acid sequence in the light chain variable regions or homologues thereof:

```
(HG-HYB 7-5)
                                        SEQ ID NO 1
DIVMTQSTAL MAASPGEKVT ITCSVSSSIS SSNLHWYQQK

SETSPKSWIY GTSNLASGVP GRFSGSGSGT SYSLTISSVE

AEDAATYYCQ QWSSYPLTFG GGTKLEIK (HG-HYB 7-14)
                                        SEQ ID NO 2
DIVLTQSPSY LAASPGETIT INCRASKSIS KYLAWYQERP

GKTNKLLIYS GSTLQSGIPS RFSGSGSGTD FTLTISSLEP

EDFAMYYCQQ HNEYPFTFGA GTKLELK
```

Preferred antibodies of the present invention may have the following amino-acid sequence in the heavy chain variable regions or homologues thereof:

```
(HG-HYB 7-5)
                                        SEQ ID NO 3
EVQLQQSGPE LVKPGASVKL SCKTSGYTFT SYDMNWVKQR

PGQGLEWIGW IFPRDGSTKF NEKFKGKATL TVDTSSTTAY

MELHSLTSED SAVYFCARAE IFFDYGFDYW GQGTTLTVSS (HG-HYB 7-14)
                                        SEQ ID NO 4
EVKVVESGGG LVQPGGSLRL SCATSGFTFS DFYMEWVRQP

PGKRLEWIAA SRNKANDYTT EYSASVKGRF IVSRDTSQSI

LYLQLNALRA EDTAIYYCAR NYYDSSYWYF DVWGAGTTVT VSS
```

Preferred antibodies of the present invention may have the following DNA sequence in the light chain variable regions or homologues thereof:

```
(HG-HYB 7-5)
                                        SEQ ID NO 5
cDNA level for light chain variable region
GACATTGTGATGACCCAGTCTACAGCACTCATGGCTGCATCTCCAGGGGAG

AAGGTCACCATCACCTGCAGTGTCAGCTCAAGTATAAGTTCCAGCAACTTG

CACTGGTACCAGCAGAAGTCAGAAATCCCCCAAATCCTGGATTTATGGCAC

ATCCAACCTGGCTTCTGGAGTCCCTGGTCGCTTCAGTGGCAGTGGATCTGG

GACCTCTTATTCTCTCACAATCAGCAGCGTGGAGGCTGAAGATGCTGCCCT

ATTACTGTCAACAGTGGAGTAGTTACCCACTGACGTTCGGTGGAGGCACCA

AGCTGGAAATCAAA (HG-HYB 7-14)
                                        SEQ ID NO 6
cDNA level for light chain variable region
GACATTGTGCTGACCCAATCTCCATCTTATCTTGCTGCATCTCCTGGAGAA

ACCATTACTATTAATTGCAGGGCAAGTAAGAGCATTAGCAAATATTTAGCC

TGGTATCAAGAGAGACCTGGGAAAAAATAAACTTCTTATCTATTCTGGATC

CACTTTGCAATCTGGAATTCCATCAAGGTTCAGTGGCAGTGGATCTGGTAC

AGATTTCACTCTCACCATCAGTAGCCTGGAGCCTGAAGATTTTGCAATGAT

ACTGTCAACAGCATAATGAATATCCGTTCACGTTCGGTGCTGGGACCAAGC

TGGAGCTGAAA
```

Preferred antibodies of the present invention may have the following DNA sequence in the heavy chain variable regions or homologues thereof:

```
(HG-HYB 7-5)
                                        SEQ ID NO 7
cDNA level for heavy chain variable region
GAGGTGCAGCTGCAGCAGTCAGGACCTGAGCTGGTGAAGCCTGGGGCTTCA

GTGAAGTTGTCCTGCAAGACTTCTGGCTACACCTTCACAAGCTACGATATG

AACTGGGTGAAACAGAGGCCTGGACGGACTTGAGTGGATTGGTTGGATTTT

TCCTAGAGATGGTAGTACTAAGTTCAATGAGAAGTTCAAGGGCAAGGCCAC

ATTGACTGTAGACACATCCTCCACCACAGCGTACATGGAACTCCACAGCTA

CATCTGAGGACTCTGCGGTCTATTTCTGTGCAAGAGCGGAGATCTTCTTTG

ATTACGGCTTTGACTACTGGGGCCAAGGCACCACTCTCACAGTCTCCTCA
```

-continued (HG-HYB 7-14)
SEQ ID NO 8
cDNA level for heavy chain variable region
GAGGTGAAGGTGGTGGAATCTGGAGGAGGCTTGGTACAGCCTGGGGGTTCT

CTGAGACTCTCCTGTGCAACTTCTGGGTTCACCTTCAGTGATTTCTACATG

GAGTGGGTCCGCCAGCCTCCAGGGAAGACTGGAGTGGATTGCTGCAAGTAG

AAACAAAGCTAATGATTATACAACAGAGTACAGTGCATCTGTGAAGGGTCG

GTTCATCGTCTCCAGAGACACTTCCCAAAGCATCCTCTACCTTCAGCTGAA

TGCCCTGAGAGCTGAGGACACTGCCATTTATTACTGTGCAAGAAATTACTA

CGATAGTAGCTACTGGTACTTCGATGTCTGGGGCGCAGGGACCACGGTCAG

TCTCCTCA

Further antibodies of the present invention may have the following amino-acid sequence in the heavy chain variable regions or homologues thereof:

(HYBR7_1_H-2_M13_F_B01.seq)
SEQ ID NO 9
LPEVQLEESGADLVKPGTSVKLSCKASGFTFTSYWMHWVKQRPGQGLEWIG

VIHPNSGNTKYNEKFRSEATLTVDKSSNTAYIQLSSLTSEDSAVYYCAREM

WNYGNSVVYFDVWGTGTTVTVSSAKTTPPSVYS (HYBR7_1_H-7_M13_F_G01.seq)
SEQ ID NO 10
LPQVKLEESGADLVKPGTSVKLSCKASGFTFTSYWMHVVVKQRPGQGLEWI

GVIHPNSGNTKYNEKFRSEATLTVDKSSNTAYIQLSSLTSEDSAVYYCARE

MWNYGNSVVYFDVWGTGTTVTVSSAKTTPPSVYS (HYBR7_1_H-9_M13_F_A02.seq)
SEQ ID NO 11
LPEVQLEESGADLVKPGTSVKLSCKASGFTFTSYWMHVVVKQRPGQGLEWI

GVIHPNSGNTKYNEKFRSEATLTVDKSSNTAYIQLSSLTSEDSAVYYCARE

MWNYGNSVVYFDVWGTGTTVTVSSAKTTPPSVYS

These further sequences may have the following amino-acid sequence in the light chain variable regions or homologues thereof:

(HYBR7_1_L-2_M13_F_F02.seq)
SEQ ID NO 12
DIVLTQTPASLAVSLGQRATISYRASKSVSTSGYSYMHWNQQKPGQPPRLL

IYLVSNLESGVPARFSGSGSGTDFTLNIHPVEEEDAATYYCQHIRELTRSE

GGPSWK*NGLMLHQLYP (HYBR7_1_L-4_M13_F_H02.seq)
SEQ ID NO 13
DIVLTQTPASLAVSLGQRATISYRASKSVSTSGYSYMHWNQQKPGQPPRL

LIYLVSNLESGVPARFSGSGSGTDFTLNIHPVEEEDAATYYCQHIRELTR

SEGGPSWK*NGLMLHQLYP (HYBR7_1_L-6_M13_F_B03.seq)
SEQ ID NO 14
DIVITQTPASLAVSLGQRATISYRASKSVSTSGYSYMHWNQQKPGQPPRLL

IYLVSNLESGVPARFSGSGSGTDFTLNIHPVEEEDAATYYCQHIRELTRSE

GGPSWK*NGLMLHQLYP

These further sequences may have the following DNA sequence in the heavy chain variable regions or homologues thereof:

(HYBR7_1_H-2_M13_F_B01.seq)
cDNA level for heavy chain variable region
SEQ ID NO 15
CTTCCGGAGGTACAGCTGGAGGAGTCAGGGGCTGACCTGGTAAAGCCTGGG

ACTTCAGTGAAATTGTCCTGCAAGGCTTCTGGCTTCACTTTCACCAGCTAC

TGGATGCACTGGGTGAAGCAGAGGCCTGGACAAGGCCTTGAGTGGATTGGA

GTGATTCATCCTAACAGTGGTAATACTAAGTACAATGAAAAATTCAGGAGT

GAGGCCACACTGACAGTAGACAAGTCCTCCAACACAGCCTACATACAACTC

AGCAGCCTGACATCTGAGGACTCTGCGGTCTATTACTGTGCAAGAGAGATG

TGGAACTACGGTAATAGCTGGTATTTCGATGTCTGGGGCACAGGGACCACG

GTCACCGTCTCCTCAGCCAAAACGACACCCCCATCTGTCT

ATTCC (HYBR7_1_H-7_M13_F_G01.seq)
cDNA level for heavy chain variable region
SEQ ID NO 16
CTTCCGCAAGTCAAGCTGGAGGAGTCAGGGGCTGACCTGGTAAAGCCTGGG

ACTTCAGTGAAATTGTCCTGCAAGGCTTCTGGCTTCACTTTCACCAGCTAC

TGGATGCACTGGGTGAAGCAGAGGCCTGGACAAGGCCTTGAGTGGATTGGA

GTGATTCATCCTAACAGTGGTAATACTAAGTACAATGAAAAATTCAGGAGT

GAGGCCACACTGACAGTAGACAAGTCCTCCAACACAGCCTACATACAACTC

AGCAGCCTGACATCTGAGGACTCTGCGGTCTATTACTGTGCAAGAGAGATG

TGGAACTACGGTAATAGCTGGTATTTCGATGTCTGGGGCACAGGGACCACG

GTCACCGTCTCCTCAGCCAAAACGACACCCCCATCTGTCTATTCC (HYBR7_1_H-9_M13_F_A02.seq)
cDNA level for heavy chain variable region
SEQ ID NO 17
CTTCCGGAAGTACAGCTGGAGGAGTCAGGGGCTGACCTGGTAAAGCCTGGG

ACTTCAGTGAAATTGTCCTGCAAGGCTTCTGGCTTCACTTTCACCAGCTAC

TGGATGCACTGGGTGAAGCAGAGGCCTGGACAAGGCCTTGAGTGGATTGGA

GTGATTCATCCTAACAGTGGTAATACTAAGTACAATGAAAAATTCAGGAGT

GAGGCCACACTGACAGTAGACAAGTCCTCCAACACAGCCTACATACAACTC

AGCAGCCTGACATCTGAGGACTCTGCGGTCTATTACTGTGCAAGAGAGATG

TGGAACTACGGTAATAGCTGGTATTTCGATGTCTGGGGCACAGGGACCACG

GTCACCGTCTCCTCAGCCAAAACGACACCCCCATCTGTCTATTCC

These further sequences may have the following DNA sequence in the light chain variable regions or homologues thereof:

(HYBR7_1_L-2_M13_F_F02.seq)
cDNA level for light chain variable region
SEQ ID NO 18
CTTCCGGAGGTACAGCTGGAGGAGTCAGGGGCTGACCTGGTAAAGCCTGGG

ACTTCAGTGAAATTGTCCTGCAAGGCTTCTGGCTTCACTTTCACCAGCTAC

TGGATGCACTGGGTGAAGCAGAGGCCTGGACAAGGCCTTGAGTGGATTGGA

GTGATTCATCCTAACAGTGGTAATACTAAGTACAATGAAAAATTCAGGAGT

```
GAGGCCACACTGACAGTAGACAAGTCCTCCAACACAGCCTACATACAACTC

AGCAGCCTGACATCTGAGGACTCTGCGGTCTATTACTGTGCAAGAGAGATG

TGGAACTACGGTAATAGCTGGTATTTCGATGTCTGGGGCACAGGGACCACG

GTCACCGTCTCCTCAGCCAAAACGACACCCCCATCTGTCTATTCC (HYBR7_1_L-4_M13_F_H02.seq)
cDNA level for light chain variable region
                                            SEQ ID NO 19
CTTCCGCAAGTCAAGCTGGAGGAGTCAGGGGCTGACCTGGTAAAGCCTGGG

ACTTCAGTGAAATTGTCCTGCAAGGCTTCTGGCTTCACTTTCACCAGCTAC

TGGATGCACTGGGTGAAGCAGAGGCCTGGACAAGGCCTTGAGTGGATTGGA

GTGATTCATCCTAACAGTGGTAATACTAAGTACAATGAAAAATTCAGGAGT

GAGGCCACACTGACAGTAGACAAGTCCTCCAACACAGCCTACATACAACTC

AGCAGCCTGACATCTGAGGACTCTGCGGTCTATTACTGTGCAAGAGAGATG

TGGAACTACGGTAATAGCTGGTATTTCGATGTCTGGGGCACAGGGACCACG

GTCACCGTCTCCTCAGCCAAAACGACACCCCCATCTGTCTATTCC (HYBR7_1_L-6_M13_F_B03.seq)
cDNA level for light chain variable region
                                            SEQ ID NO 20
CTTCCGGAAGTACAGCTGGAGGAGTCAGGGGCTGACCTGGTAAAGCCTGGG

ACTTCAGTGAAATTGTCCTGCAAGGCTTCTGGCTTCACTTTCACCAGCTAC

TGGATGCACTGGGTGAAGCAGAGGCCTGGACAAGGCCTTGAGTGGATTGGA

GTGATTCATCCTAACAGTGGTAATACTAAGTACAATGAAAAATTCAGGAGT

GAGGCCACACTGACAGTAGACAAGTCCTCCAACACAGCCTACATACAACTC

AGCAGCCTGACATCTGAGGACTCTGCGGTCTATTACTGTGCAAGAGAGATG

TGGAACTACGGTAATAGCTGGTATTTCGATGTCTGGGGCACAGGGACCACG

GTCACCGTCTCCTCAGCCAAAACGACACCCCCATCTGTCTATTCC
```

Additional antibodies of the present invention may have the following amino-acid sequence in the heavy chain variable regions or homologues thereof:

```
(HYBR7_6_H-1_M13_F_A04.seq)
                                            SEQ ID NO 21
LPEVQLEESGPGLVAPSQSLSITCTVSGFSLTRYGVHVVVRQPPGKGLEWL

GVIWTAGNTNYNSALMSRLSISKDNSKTQVFLKMNSLQTDDTAMYYCARDD

PSMAYWGQGTSVTVSSAKTTPPSVYS (HYBR7_6_H-2_M13_F_B04.seq)
                                            SEQ ID NO 22
LPQVQLEQSGPGLVAPSQSLSITCTVSGFSLTRYGVHVVVRQPPGKGLEWL

GVIWTAGNTNYNSALMSRLSISKDNSKTQVFLKMNSLQTDDTAMYYCARDD

PSMAYWGQGTSVTVSSAKTTPPSVYS (HYBR7_6_H-3_M13_F_C04.seq)
                                            SEQ ID NO 23
LPQVKLQQSGPGLVAPSQSLSITCTVSGFSLTRYGVHWVRQPPGKGLEWLG

VIWTAGNTNYNSALMSRLSISKDNSKTQVFLKMNSLQTDDTAMYYCARDDP

SMAYWGQGTSVTVSSAKTTPPSVYS
```

These additional antibodies of the present invention may have the following amino-acid sequence in the light chain variable regions or homologues thereof:

```
(HYBR7_6_L-1_M13_F_E05.seq)
                                            SEQ ID NO 24
DIVLTQTPAIMSVSPGEKVTITCSASSSVSYMHWFQQKPGTSPKLWIYSTS

NLASGVPARFSGSGSGTSYSLTISRTEAEDAATYYCQQRSSYPYTFGGGTK

LEIKRADAAPTVST (HYBR7_6_L-2_M13_F_F05.seq)
                                            SEQ ID NO 25
DIVLTQTPAIMSVSPGEKVTITCSASSSVSYMHWFQQKPGTSPKLWIYSTS

NLASGVPARFSGSGSGTSYSLTISRTEAEDAATYYCQQRSSYPYTFGGGTK

LEIKRADAAPTVST (HYBR7_6_L-3_M13_F_G05.seq)
                                            SEQ ID NO 26
DIVLTQTPAIMSVSPGEKVTITCSASSSVSYMHWFQQKPGTSPKLWIYSTS

NLASGVPARFSGSGSGTSYSLTISRTEAEDAATYYCQQRSSYPYTFGGGTK

LEIKRADAAPTVST
```

These additional sequences may have the following DNA sequence in the heavy chain variable regions or homologues thereof:

```
(HYBR7_6_H-1_M13_F_A04.seq)
cDNA level for heavy chain variable region
                                            SEQ ID NO 27
CTTCCGGAGGTGCAGCTGGAGGAGTCAGGACCTGGCCTGGTGGCGCCCTCA

CAGAGCCTGTCCATCACTTGCACTGTCTCTGGATTTTCATTAACCAGATAT

GGTGTACACTGGGTTCGCCAGCCTCCAGGAAAGGGTCTGGAGTGGCTGGGA

GTAATCTGGACTGCTGGAAACACAAATTATAATTCGGCTCTCATGTCCAGA

CTGAGCATCAGCAAAGACAACTCCAAGACCCAAGTTTTCTTAAAAATGAAC

AGTCTCCAAACTGATGACACAGCCATGTACTACTGTGCCAGAGATGATCCC

TCTATGGCCTACTGGGGTCAAGGAACCTCAGTCACCGTCTCCTCAGCCAAA

ACGACACCCCCATCTGTCTATTCC (HYBR7_6_H-2_M13_F_B04.seq)
cDNA level for heavy chain variable region
                                            SEQ ID NO 28
CTTCCGCAAGTACAGCTGGAGCAGTCAGGACCTGGCCTGGTGGCGCCCTCA

CAGAGCCTGTCCATCACTTGCACTGTCTCTGGATTTTCATTAACCAGATAT

GGTGTACACTGGGTTCGCCAGCCTCCAGGAAAGGGTCTGGAGTGGCTGGGA

GTAATCTGGACTGCTGGAAACACAAATTATAATTCGGCTCTCATGTCCAGA

CTGAGCATCAGCAAAGACAACTCCAAGACCCAAGTTTTCTTAAAAATGAAC

AGTCTCCAAACTGATGACACAGCCATGTACTACTGTGCCAGAGATGATCCC

TCTATGGCCTACTGGGGTCAAGGAACCTCAGTCACCGTCTCCTCAGCCAAA

ACGACACCCCCATCTGTCTATTCC (HYBR7_6_H-3_M13_F_C04.seq)
cDNA level for heavy chain variable region
                                            SEQ ID NO 29
CTTCCGCAGGTAAAGCTGCAGCAGTCTGGACCTGGCCTGGTGGCGCCCTCA

CAGAGCCTGTCCATCACTTGCACTGTCTCTGGATTTTCATTAACCAGATAT

GGTGTACACTGGGTTCGCCAGCCTCCAGGAAAGGGTCTGGAGTGGCTGGGA

GTAATCTGGACTGCTGGAAACACAAATTATAATTCGGCTCTCATGTCCAGA

CTGAGCATCAGCAAAGACAACTCCAAGACCCAAGTTTTCTTAAAAATGAAC
```

-continued

```
AGTCTCCAAACTGATGACACAGCCATGTACTACTGTGCCAGAGATGATCCC

TCTATGGCCTACTGGGGTCAAGGAACCTCAGTCACCGTCTCCTCAGCCAAA

ACGACACCCCCATCTGTCTATTCC
```

These additional sequences may have the following DNA sequence in the light chain variable regions or homologues thereof:

```
(HYBR7_6_L-1_M13_F_E05.seq)
cDNA level for light chain variable region
                                       SEQ ID NO 30
GGGACATTGTGCTGACCCAAACTCCAGCAATCATGTCTGTATCTCCAGGGG

AGAAGGTCACCATAACCTGTAGTGCCAGCTCAAGTGTAAGTTACATGCACT

GGTTCCAGCAGAAGCCAGGCACTTCTCCCAAACTCTGGATTTATAGCACAT

CCAACCTGGCTTCTGGAGTCCCTGCTCGCTTCAGTGGCAGTGGATCTGGGA

CCTCTTACTCTCTCACAATCAGCCGAACGGAGGCTGAAGATGCTGCCACTT

ATTACTGCCAACAAGGAGTAGTTACCCGTACACGTTCGGAGGGGGGACCA

AGCTGGAAATAAAACGGGCTGATGCTGCACCAACTGTATCCACC (HYBR7_6_L-2_M13_F_F05.seq)
cDNA level for light chain variable region
                                       SEQ ID NO 31
GGGATATTGTGCTCACACAAACTCCAGCAATCATGTCTGTATCTCCAGGGG

AGAAGGTCACCATAACCTGTAGTGCCAGCTCAAGTGTAAGTTACATGCACT

GGTTCCAGCAGAAGCCAGGCACTTCTCCCAAACTCTGGATTTATAGCACAT

CCAACCTGGCTTCTGGAGTCCCTGCTCGCTTCAGTGGCAGTGGATCTGGGA

CCTCTTACTCTCTCACAATCAGCCGAACGGAGGCTGAAGATGCTGCCACTT

ATTACTGCCAACAAGGAGTAGTTACCCGTACACGTTCGGAGGGGGGACCA

AGCTGGAAATAAAACGGGCTGATGCTGCACCAACTGTATCCACC (HYBR7_6_L-3_M13_F_G05.seq)
cDNA level for light chain variable region
                                       SEQ ID NO 32
GGGACATTGTGCTCACACAGACTCCAGCAATCATGTCTGTATCTCCAGGGG

AGAAGGTCACCATAACCTGTAGTGCCAGCTCAAGTGTAAGTTACATGCACT

GGTTCCAGCAGAAGCCAGGCACTTCTCCCAAACTCTGGATTTATAGCACAT

CCAACCTGGCTTCTGGAGTCCCTGCTCGCTTCAGTGGCAGTGGATCTGGGA

CCTCTTACTCTCTCACAATCAGCCGAACGGAGGCTGAAGATGCTGCCACTT

ATTACTGCCAACAAGGAGTAGTTACCCGTACACGTTCGGAGGGGGGACCA

AGCTGGAAATAAAACGGGCTGATGCTGCACCAACTGTATCCACC
```

The monoclonal antibodies may be coupled to a detectable label or a substance having toxic or therapeutic activity.

The present invention also provides a method of making a hybridoma cell line producing a monoclonal antibody that blocks the integrin interacting motif in MFAP4 of human microfibrillar-associated protein 4 (MFAP4) comprising:
(a) providing suitable animal for raising monoclonal antibody against human MFAP4, such as a MFAP4 knockout mouse;
(b) injecting the animal with human MFAP4; and
(c) obtaining hybridoma cells from the mouse wherein the hybridoma cells produce a monoclonal antibody against human MFAP4, said monoclonal blocks the integrin interacting motif in MFAP4 of human microfibrillar-associated protein 4 (MFAP4).

DESCRIPTION OF THE FIGURES

FIG. 4 shows MFAP4 induced VSMC migration and proliferation is inhibited by MFAP4 blocking anti-bodies in vitro. (A) fHAoSMCs were seeded in poly-D-lysine (PDL, negative control), or rMFAP4 coated micro-well plates with a central rounded area blocked by a cell stopper. The number of flourescently labelled cells was counted within this central area of the well (depicted) twenty hrs after removal of the cell stoppers and ±the anti-MFAP4 antibodies HG-HYB 7-5 (7-5), HG-HYB 7-14 (7-14), HG-HYB 7-18 (7-18), or isotype control antibodies (iso) in order to quantitate cellular migration. (B) Cell counts from the migrations assay were performed using no coating (blank), PDL-, rMFAP4-, or fibronection-coating and (C) using rMFAP4 coating in the presence of antibodies. The data are representative for 3 individual experiments, with observations made in quadruplicates. The data (B and C) are means+SEM obtained from two of these experiments. (D-E) The colourimetric MTT-assay was used to quantitate fHAoSMC proliferation. (D) fHAoSMCs were seeded in tissue culture wells with no coating (blank), rMFAP4-coating, or fibronectin-coating and + (black) or − (grey) PDGF-BB treatment 48 hrs after seeding. (E) fHAoSMCs were seeded in tissue culture wells with rMFAP4-coating±PDGF-BB treatment after preincubation with anti-MFAP4 antibodies. Data are means+SEM measured in triplicates and representative for at least two different experiments.

DETAILED DESCRIPTION OF THE INVENTION

Figure 1:
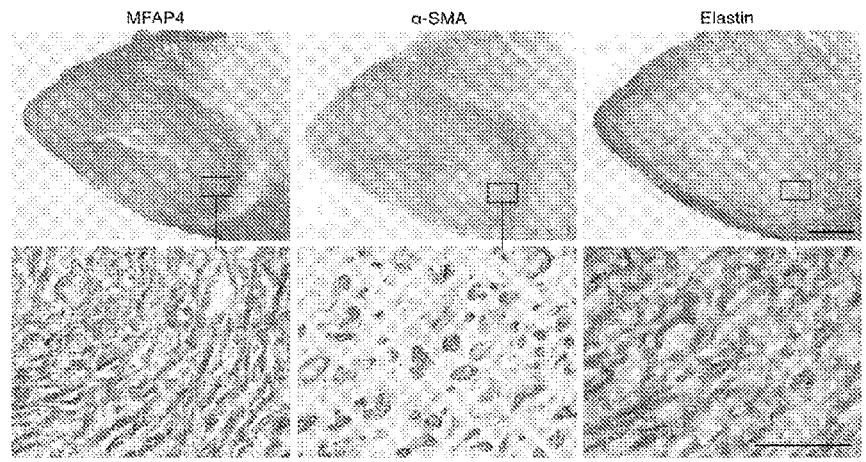
FIG. 1 shows Immunohistochemical detection of MFAP4 in sections from a human vein with smooth muscle cell hyperplasia. MFAP4 and α-SMA were visualized by immunostaining, and elastin was visualized using Weigert's elastin stain. Upper panel, original magnification 25×. Lower panel, original magnification 1000×.

MFAP4 Cross/Inks VSMCs to ECM Fibrils and Induces Cellular Migration and Proliferation Through Integrin $\alpha_v\beta_3$/$\beta_5$ Ligation In order to elucidate the presence of MFAP4 in human vascular tissue with patological remodeling processes sections from a human vein with intimal hyperplasia were obtained from a patient with lower extremity PAD that underwent surgical reconstitution following bypass surgery induced restenosis. The neointima appeared with inhomogenous staining for MFAP4. The most intense MFAP4 staining was localized closest to the outer periphery of the vessel. A similar staining pattern was found for both α-smooth muscle actin (α-SMA) and elastin. MFAP4 staining appeared to colocalize with the elastic fibers, whereas the α-SMA staining was intracellular (FIG. 1). Immunostaining detected dispersed integrin $\alpha_v\beta_3$ staining throughout the neointimal area with highest intensity in capillary endothelium. Few intervening CD45-positive inflammatory cells were also observed.

Figure 2:
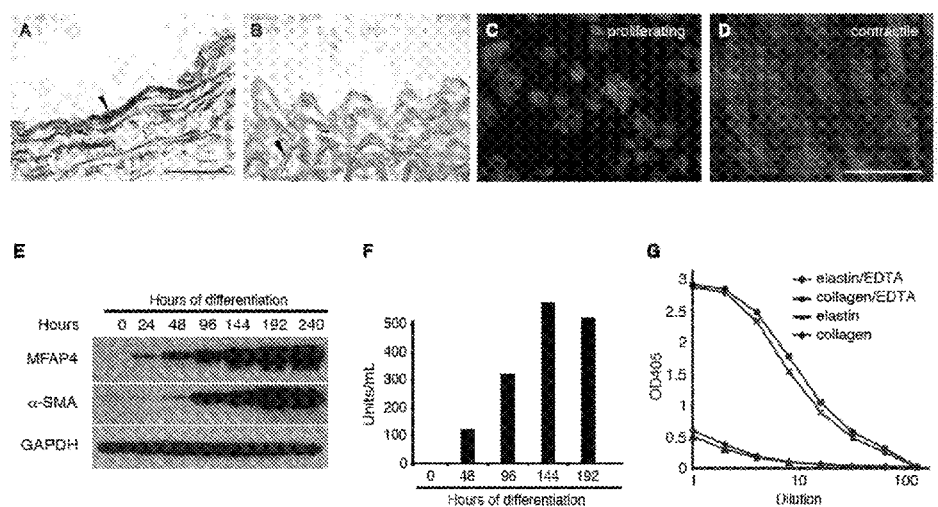
FIG. 2 shows MFAP4 is expressed in elastic vessels, regulated MFAP4 synthesis is found in VSMCs, and secreted MFAP4 binds ECM fibrils in the vessel wall. Immunohistochemal staining of (A) human mammary artery and (B) mouse aorta with a monoclonal anti-MFAP4 antibody (HG Hyb 7-14). Brown indicates positive staining. Arrowheads indicate the lamina elastica interna as well as elastic structures in media and arrows indicate the intervening VSMCs. FHAoSMCs grown in media supporting either proliferation (C) or differentiation (D) stained with FITC-labelled anti-MFAP4-antibodies (HG Hyb 7-14) and DAPI. (E) Semiquantitative Western Blotting analysis of MFAP4 from fHAoSMC lysates, which differentiate from the synthezising/proliferating phenotype to the contractile/differentiating phenotype in a time series using α-SMA as a marker for induction of the contractile/differentiating phenotype. The amount of loaded protein was normalized to GAPDH. (F) The concentration of MFAP4 in cell culture media from the same experiment as in (E) measured by ELISA. (G) Pull-down of rMFAP4 by collagen type 1 or by elastin in the presence of calcium or EDTA. After pull-down of the insoluble fibrils and centrifugation the supernatants were analysed for MFAP4 by ELISA. Data are means from experimental duplicates and representative of at least three independent experiments.

Following the inventors demonstrated a high intense immunohistochemical staining for MFAP4 and localization to elastic fibers within the normal human mammary artery (FIG. 2A) and mouse aorta (FIG. 2B). A similar staining pattern was found throughout all investigated peripheral muscularized blood vessels from a human organ multi-block. MFAP4 synthesis and secretion from fHAoSMC's were observed using cytoimmunohistochemistry (FIG. 2C, 2D), Western Blotting (FIG. 2E) and by enzyme-linked immunosorbent assay (ELISA) quantification in the cell culture supernatant. Moreover, both cellular associated (FIG. 2C-E) and secreted (FIG. 2F) MFAP4 was increased several fold in parallel with the known marker of differentiation α-SMA during >100 hrs shift from a proliferative phenotype and into a contractile phenotype in the culture. Pull-down experiments were used to detect direct interaction between recombinant MFAP4 (rMFAP4) and collagen or elastin in a $Ca^{2+}$-dependent manner (FIG. 2G) suggesting that the binding takes place through the conserved S1-binding site in the FReD.

Figure 3:
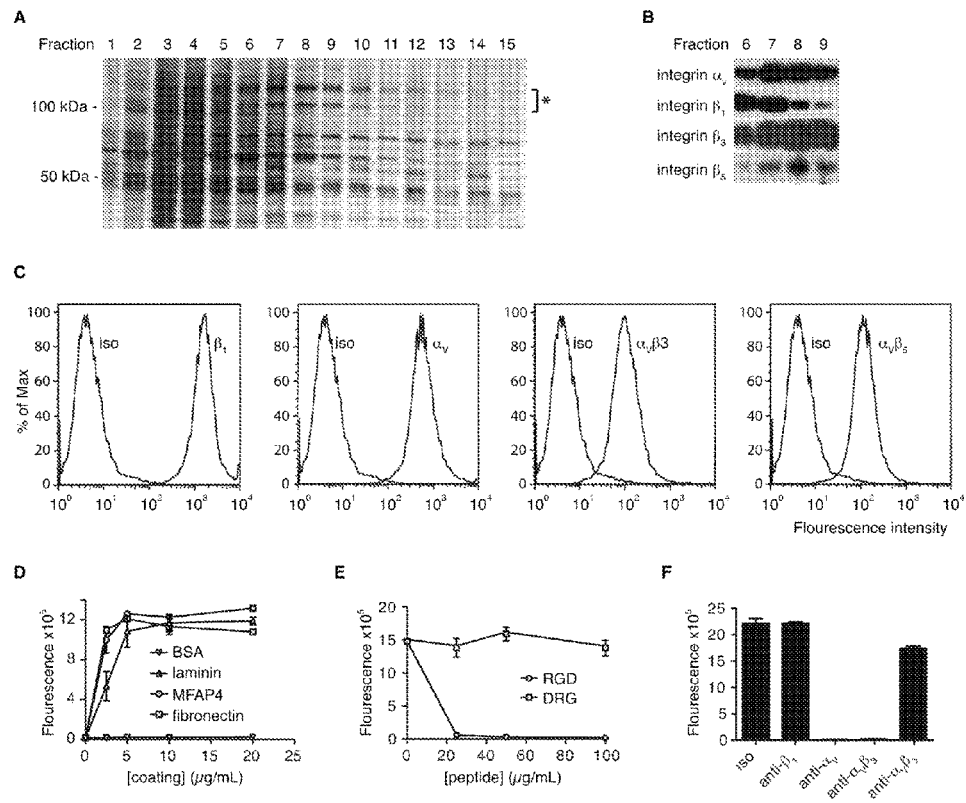
FIG. 3 shows identification of integrin receptors for MFAP4. (A) Silverstained elution profile for human placenta membrane proteins purified using an rMFAP4 coupled matrix. The double bands around 100 kDa labelled with and asterix represent potentially eluted integrins. (B) Immuno-detection of integrins eluted in fractions 6-9 from (A) by Western Blotting using anti-integrin $\alpha_V$, $\beta_1$, $\beta_3$, or $\beta_5$ specific antibodies. (C) FACS analysis of fHAoSMCs using FITC-labelled anti-integrin $\alpha_V$, $\beta_1$, $\beta_3$, $\beta_5$ or isotype control (iso) specific antibodies. (D) Adhesion assay assessing attachment of flourescently labelled fHAoSMCs onto various concentrations of immobilized BSA, laminin, rMFAP4, or fibronectin, respectively. (E) Adhesion assay assessing attachment of fHAoSMCs onto one fixed concentration of immobilized rMFAP4 in competition with integrin inhibitory RGD-containing peptide or DRG-containing control peptide, respectively. (F) Adhesion assay assessing attachment of fHAoSMCs onto one fixed concentration of immobilized rMFAP4 in competition with integrin-blocking anti-bodies specifically directed against integrins $\beta_1$, $\alpha_V$, $\alpha_V\beta_3$, or $\alpha_V\beta_5$, respectively. Data points are means+SEM from experimental triplicates and representative for at least two independent experiments.

To identify relevant MFAP4 binding integrins, human placenta membrane proteins were affinity purified on immobilized rMFAP4. Proteins, which might correspond to integrins according to molecular weight, were eluted from the column and integrin monomers $α_V$, $β_1$, $β_3$, and $β_5$ were detected specifically in the collected fractions (FIGS. 3A and B). Similar results were obtained using fluorescence-activated cell sorting (FACS) analysis of fHAoSMC (FIG. 3C). A cellular adhesion assay following demonstrated that calcein AM fluorogenic dye labeled fHAoSMCs attached to rMFAP4, fibronectin, and laminin and failed to adhere to bovine serum albumin (BSA) (FIG. 3D). The synthetic peptide GRGDSP completely inhibited cellular attachment of to rMFAP4, whereas the control peptide SDGRG showed no significant inhibition (FIG. 3E). Anti-integrin $α_V$ and anti-integrin $α_Vβ_3$ antibodies completely blocked the cellular adhesion to rMFAP4, while anti-integrin $α_Vβ_5$ antibodies showed a small but significant reduction in adhesion. In contrast, anti-integrin $β_1$ had no effect on the cellular adhesion to rMFAP4 (FIG. 3F). The integrins were detectable through all tested cel culture conditions. Yet, integrin $α_V$ and integrin $β_5$ were coordinately expressed with MFAP4 while integrin $β_3$ expression was diminished when fHAoSMCs differentiated from the proliferating to the contractile phenotype.

Monoclonal Anti-MFAP4 Antibodies Block VSMC Interaction with MFAP4

Monoclonal anti-MFAP4 antibodies were raised in mfap4−/− mice because the mouse MFAP4 homologue has very high sequence similarity to certain regions within the human protein. ELISA based assays demonstrated that produced antibodies with reactivity against MFAP4; anti-MFAP4 HG-Hyb 7-14 and 7-18 antibodies clearly bind double (AGA) and triple (AAA) RGD mutated rMFAP4 in the chinese hamster ovary (CHO) cell culture supernatant. In contrast, the rMFAP4 detection signals were reduced for the point-mutated proteins when the HG-Hyb 7-5 was used as capture antibody suggesting that HG-Hyb 7-5 binds to an epitope covering the RGD sequence in rMFAP4. HG-HYB 7-5 and HG-HYB 7-14 both prohibited the cellular adhesion to rMFAP4. This latter observation suggests that HG-HYB 7-14 may bind at close proximity to the RGD site. It was further observed that focal adhesions and cellular stress fibers (vinculin and F-actin, respectively) formed within 20 hrs of exposure to either fibronectin or rMFAP4, but not with poly-D-lysin. Inhibition of focal adhesion and stress fiber formation was observed when fHAoSMCs were incubated with the blocking antibodies.

Cellular Migration and Proliferation of VSMCs are Induced by MFAP4 and Inhibited by MFAP4 Blocking Antibodies The fHAoSMC migration was increased almost 2-fold towards immobilized rMFAP4 (FIGS. 4A and B). Incubation with HG-HYB 7-5 or 7-14 antibodies reduced the numbers of migrating cells significantly while no effect was seen when using the non-blocking HG-HYB 7-18 antibody or the isotype control (FIGS. 4A and C).

The effect of rMFAP4 on proliferating fHAoSMC was further assessed using a Thiazoyl blue tetra-zolium bromide (MTT)-assay. The cells were allowed to proliferate for 48 hrs, either in the presence or absence of 5 ng/mL platelet-derived growth factor-BB (PDGF-BB) and the proliferation was significantly induced when cells were seeded onto either rMFAP4 or fibronectin (FIG. 4D). Microplates coated with rMFAP4 were following blocked with anti-MFAP4 antibodies before seeded with fHAoSMC. HG-HYB 7-5 and 7-14 both lead to a significant reduction of cellular proliferation to a non-PDGF-BB treated level (FIG. 4E) in parallel with integrin $α_Vβ_3$ blocking antibodies (data not shown).

Generation and Characterization of MFAP4 Deficient Mice

Figure 5:
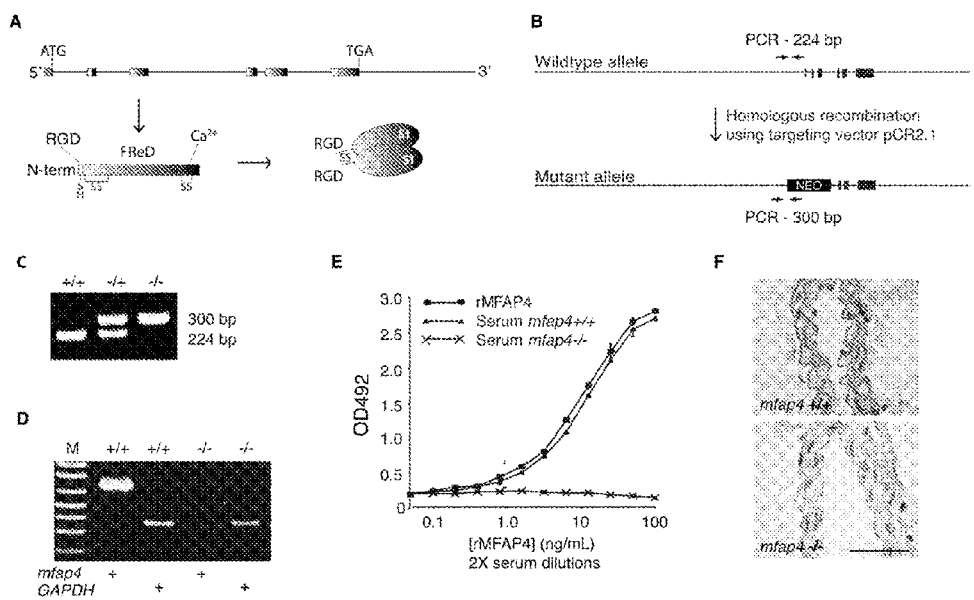
FIG. 5 shows generation of MFAP4 deficient mice. (A) The MFAP4 gene product is transcribed from 6 exons on chromosome 17. The mature protein comprises an N-terminal region including one free sulfhydryl-group and RGD integrin binding sequence. (B) The wild-type mfap4 allele was used to produce the targeting vector. The targeting vector was designed to exclude a region of 1.5 kb of the non-coding 5' region and the first three exons of the mfap4 gene by exclusion of a EcoRI fragment and replacing it with the PGKneo expression cassette. The lower diagram illustrates the mutated allele. (C) Duplex PCR analysis on genomic DNA from wild-type and gene-deleted mouse tails. (D) RT-PCR analysis of mfpa4 and GAPDH gene transcription from wild-type and gene deleted mouse pulmonary tissue. (E) Quantitative ELISA on 2-fold dilutions of serum from mfap4+/+ and mfap4−/− mice compared to rMFAP4. (F) Immunohiostochemical analysis on arterial tissue from mfap4+/+ and mfap4−/− mice developed with anti-MFAP4 antibody (HG-HYB 7-14).

The MFAP4 gene comprises 6 exons coding for the globular FReD and a short N-terminal sequence with a free cysteinyl-group for disulphide bridging of dimers (FIG. 5A). Mfap4−/− mice were generated on the CJ7 background using insertion of a neomycin cassette into the mfap4 gene replacing exon 1-3 coding for the RGD containing N-terminal domain and a part of the FReD (FIG. 5B). Deletion was confirmed by Southern Blotting analysis. Additional genotyping by PCR confirmed the presence of a 300 bp gene-deficient fragment and a 224 bp wild-type fragment present in mfap4−/− and mfap4+/+ derived mice (FIG. 5C). Moreover, RT-PCR analysis using pulmonary tissue lysate demonstrated the lack of mfap4 transcription in the mfap4−/− mice (FIG. 5D). Homozygous mfap4−/− mice were viable, bred with normal Mendelian frequencies, and appeared indistinguishable from wild-type littermates. Serum samples were obtained from mice in the $10^{th}$ generation. Parallelism was observed between the recombinant mouse MFAP4 and the wild-type ELISA signal (FIG. 5E). MFAP4 was absent from the mfap4−/− circulation and immunohistochemical analysis demonstrated a clear lack of detectable signals from mfap4−/− mouse tissue.

A role for MFAP4 in the assembly of microfibrils is previously suggested (34) but the elastic laminae in the arteries appeared with smooth organized lamellar sheets suggesting that the integrity of the vessel wall was preserved. The unchallenged mfap4−/− mice appeared with normal heart rate, normal blood pressure, normal circulating cell numbers, and normal blood lipid levels. The resting mean arterial blood pressure (MAP) obtained using chronic indwelling catheters placed in the femoral artery and vein was stable and averaged 98.8±2.7 mmHg and the heart rate (HR) 664±18 bpm in wild-type animals. In mfap4−/− mice MAP averaged 105.5±3.6 mmHg and the HR 661±13 bpm. Phenylephrine caused a significant increase in MAP (149.5±5.1 mmHg and 153.1±4.2 mmHg) and a corresponding decrease in HR; 442±40 bpm and 428±27 bpm, in mfap4+/+ and mfap4−/− mice respectively. There was no significant difference between genotypes either at basal levels or at increased blood pressure.

Figure 6:
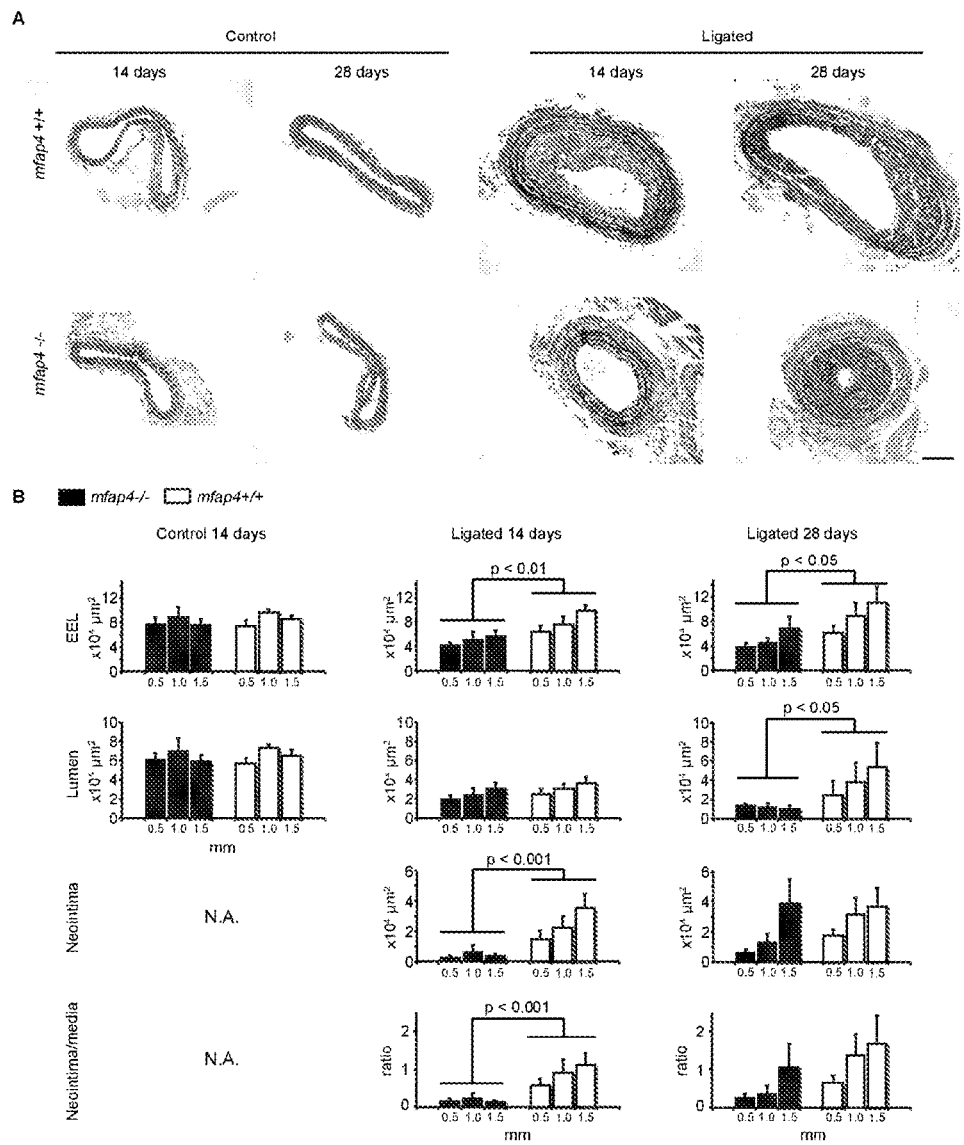
FIG. 6 shows MFAP4 accelerates neointima formation and outward remodelling of the arterial wall. (A) The left common carotid artery was ligated at the bifurcation in both mfap4+/+ (+/+) and mfap4−/− (−/−) mice and the right common carotid artery was used as unligated control. At day 14 or day 28 after ligation the vessels were dissected, fixed and obtained sections were elastin stained. The shown sections are obtained 1.5 mm distal to the bifurcation/ligation. (B) Morphometric analyses of cross sectional vessel areas were performed in unligated control carotid arteries and in the ligated carotid arteries 14 (n=6 mice/group) or 28 (n=3-6 mice/group) days after ligation. The ratios between the neointimal areas and the medial areas are depicted in the bottom panel. EEL=External elastic lamina. Black=mfap4−/− mice, white=mfap4+/+ mice. Data are means+SEM.

Decreased Vessel Diameter and Neointima Formation in Mfap4−/− Mice after Carotid Artery Ligation is Associated with Reduced VSMC Proliferation and Infiltration with CD45 Positive Cells A ligated carotid artery will undergo initial outward remodeling, followed by vessel shrinkage and neointima formation, resulting in narrowing of the lumen (35). The remodeling responses 14 days and 28 days were compared after left carotid arterial ligation in mfap4+/+ and mfap4−/− littermates of the C57BL/6N strain in order to examine whether the lack of MFAP4 affected the arterial response to ligation. Transverse sections were obtained 0.5, 1.0, and 1.5 mm proximal to the ligature/bifurcation and at corresponding locations in the contralateral vessel and stained with Verhoeff-van Gieson elastin staining (FIG. 6A). Neointimal growth appeared delayed in the mfap4−/− mice, with very limited or no formation after 14 days, but with neointimal areas comparable to mfap4+/+ after 28 days (FIG. 6B). Furthermore, the external elastic lamina (EEL) of the ligated mfap4−/− vessel was significantly decreased compared to the mfap4+/+ vessel (FIG. 6B). Thus, at day 28 the lumen in mfap4−/− vessels was significantly decreased. No apparent differences in the vessel diameter or in the lumen diameter were observed in the contralateral control arteries.

A corresponding lack of outward arterial remodeling was observed 14 days after ligation with MFAP4 deficiency in the BALB/c background. Neointimal areas appeared decreased in the mfap4−/− mice, however morphometric analysis was not attempted due to rich neovascularization of the neointimal areas in both mfap4−/− and mfap4+/+ BALB/c mice.

Figure 7:
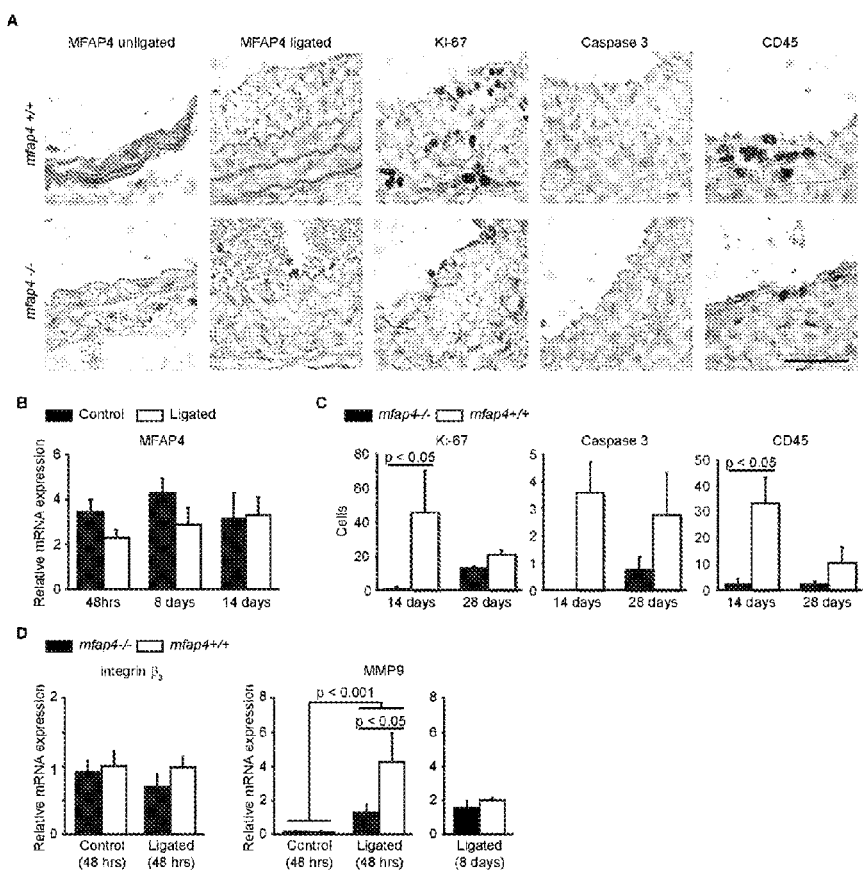
FIG. 7 shows proliferation and apoptosis of vascular cells and infiltration of inflammatory cells are decreased in mfap4−/− mice compared to mfap4+/+ mice in accordance with decreased neointima formation. (A) The MFAP4 levels, the proliferative marker Ki-67, the apoptosis marker caspase 3, and the neutrophile marker CD45 were analysed using immunohistochemical analysis on carotid arterial sections from mfap4−/− (−/−) and mfap4+/+ mice (+/+). The shown sections are obtained 1.5 mm distal to the bifurcation/ligation in mice terminated 14 days after ligation. The MFAP4 stained unligated sections are obtained from the contralateral control carotid artery. (B) The relative mfap4 mRNA expression was quantified in carotid artery samples obtained 48 hours, 8 days, or 14 days after the ligation from both control vessels and ligated mfap4+/+ vessels. Black=control, white=ligated. (C) Quantification of proliferating cells, apoptotic cells, and inflammatory cells were performed by counting the total numbers of stained cells in the media and in the neointima from sections obtained 1.5 mm distal to the bifurcation/ligation in mice terminated 14 or 28 days after ligation. Black=mfap4−/− mice, white=mfap4+/+ mice. (D) The relative expression of integrin $\beta_3$ and MMP9 mRNA was quantified in control carotid arteries or ligated carotid arteries obtained 48 hours or 8 days after the ligation was performed. Black=mfap4−/− mice, white=mfap4+/+ mice. Data are means+SEM from n=3-7 mice/group.
Figure 8:
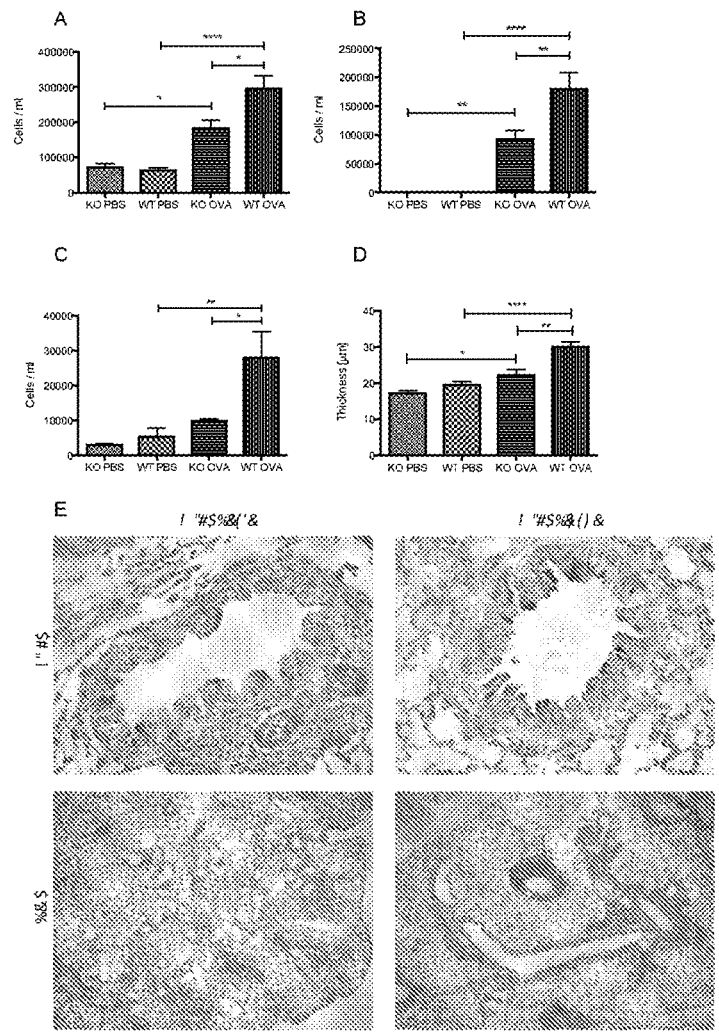
FIG. 8 shows allergic airway inflammation is attenuated in mfap4−/− mice. (A-C) Cellular infiltration into the BAL. Total cell count (A) as well as specific eosinophil (B) and neutrophil (C) numbers were lowered in mfap4−/− mice. (D-E) Histological analysis of lung parenchyma. (D) Epithelial thickness of small airways. (E) PAS (upper panel) and H-E (lower panel) stain of lungs from mfap4−/− (left) and mfap4+/+(right) mice.

Immunostaining of the ligated mfap4+/+C57BL/6N vessels revealed that MFAP4 localized to medial (most intense) as well as to neointimal cells (FIG. 7A). There was no apparent difference in MFAP4 immunohistochemical staining intensity between ligated and unligated vessels. RT-qPCR analyses of MFAP4 expression were further performed in unligated vessels, and vessels ligated for 48 hrs, 8 days, or 14 days. RT-qPCR analyses did not support significant MFAP4 regulation within this period (FIG. 7B). Highly intense immunostaining for α-SMA was likewise found in the media.

MFAP4 deficiency significantly reduced Ki-67, caspase 3, and CD45 stained cells. Ki-67 stained proliferating cells were predominantly found in the neointimal area compared to the medial area (approximately 3:1 in the mfap4+/+ vessel) (FIG. 7A), and there were no or few detectable Ki-67-stained cells in the mfap4−/− vessels at day 14 compared to mfap4+/+ vessels (1.25±0.48 (SEM) cells/section versus 45.7±24.0 (SEM) Ki-67-stained cells/section, respectively (FIG. 7C). Likewise, MFAP4 deficiency reduced the level of caspase 3 positive apoptotic cells and null cells were detected in the ligated mfap4−/− vessel by day 14 (FIG. 7C). MFAP4 deficiency further decreased the number of $CD45^+$ cells in the vessel wall significantly. The counted number was on average 33.5±10.0 (SEM) cells/section in the mfap4+/+ vessels and 2.75±1.80 (SEM) cells/section after 14 days (FIG. 7C).

RT-qPCR analyses of integrin $\beta_3$ and MMP9 were performed in control vessels and vessels ligated for 48 hrs or 8 days (for MMP9). The data did not support early or basal gene regulation of integrin $\beta_3$. In contrast, the data supported that the arterial ligation lead to significant induction of the MMP9 gene product and that MFAP4 deficiency reduced the expression. This reduction was evident 48 hrs after ligation, but disappeared during the prolonged healing response (8 days) (FIG. 7D).

Deficiency of MFAP4 Alleviates Allergic Inflammation in Murine Acute Model of Asthma To examine whether MFAP4 contributes to allergic asthma, mfap4+/+ and mfap4−/− littermates of the BALB/c strain were subjected to acute ovalbumin (OVA)-induced allergic airway disease. Leukocyte infiltration was checked in bronchoalveolar lavage (BAL), and lung tissue was evaluated for signs of inflammation and airway remodeling.

OVA-treated mfap4−/− mice exhibited significantly attenuated infiltration of neutrophils and eosinophils into the airway lumen. Moreover, analysis of histological stainings revealed more prominent parenchymal inflammation and more pronounced early airway remodeling events in VVT mice, such as increased epithelial thickness and goblet cell hyperplasia.

Data Interpretation

One mechanistic role for MFAP4 is in integrin $\alpha_V\beta_{3/5}$ activation of VSMC adhesion, migration, and proliferation. In line with this, MFAP4 deficiency delayed neointima formation after flow-cessation induced vascular injury. Yet, the lack of MFAP4 additionally reduced arterial outward remodeling and consequentially resulted in overall accelerated lumen reduction. Other roles for MFAP4 are as positive modulator of airway inflammation and airway remodeling. However, the mechanisms behind these functions remain hypothetic.

Well known integrin $\alpha_V\beta_{3/5}$ agonists often appear highly upregulated during vascular injury. In contrast to this, high vascular expression levels of MFAP4 were evident before injury and during healing responses suggesting that MFAP4 represent a novel integrin ligand with constitutive tissue expression. The systemic variation in MFAP4 levels in symptomatic obstructive PAD may thus primarily result from increased turnover of ECM.

In vitro data generated in this study identifies VSMCs as sites of synthesis for MFAP4. The localization of human MFAP4 to VSMCs combined with the observation that MFAP4 binds the ECM fibrils supported a role for MFAP4 in maintaining homeostatic functions in the vessel wall as known for other matricellular proteins and/or integrin $\alpha_V\beta_3$ ligands like osteopontin and vitronectin (29, 36, 37).

The presence of integrin receptors for MFAP4 in the VSMCs was following characterized. The utilised fetal cell line had a relatively high expression of integrin $\alpha_V\beta_3$ and therefore may represent partly dedifferentiated cells as commonly observed in ligated or otherwise injured arteries. An alternatively tested adult HAoSMC line predominantly expressed integrin $\alpha_V\beta_5$ and interacted with MFAP4 through this receptor (data not shown). The almost complete disruption of cellular adhesion onto immobilized MFAP4 with blocking antibodies strongly indicates that integrin $\alpha_V\beta_3$ is the dominating MFAP4 interaction partner in the present investigations.

The relatively high level of MFAP4 in the diseased as well as in the normal artery separates the expressional regulation of MFAP4 from the common transient high expression of matricellular proteins and well-known integrin $\alpha_V\beta_{3/5}$ ligands and suggests that MFAP4 mediated cellular effects primarily are regulated by other means than expression.

The data further demonstrated that MFAP4 induced functional distribution of integrins in focal adhesion sites as well as cellular migration, and proliferation. Such in vitro observations are well known for integrin $\alpha_V\beta_3$ ligands osteopontin and vitronectin (38, 39). The inventors observed reversal of the MFAP4 induced cellular effects in the presence of MFAP4 blocking antibodies and the observations indicated that growth factors like PDGF may determine the effect of MFAP4 induced integrin activation.

In order to study the effects of MFAP4 on VSMC biology in vivo the mouse mfap4 gene was inactivated. Histological examinations of tissues including arteries, skin and lung from unchallenged mfap4−/− mice showed a normal gross appearance up till at least 3 months of age. The mean blood pressure did not differ between wild-type, and homozygous mfap4−/− mice when measured through catheterization. Blood pressure responses to phenylephrine infusions were normal in homozygous mfap4−/− mice, indicating that the mfap4 gene deficiency did not alter the intrinsic pharmacological properties of smooth muscle cells in mice. Thus, no relevant cardiovascular phenotype was found in the unchallenged mfap4−/− mice. These observations supported that MFAP4 is not essential for survival or normal cardiovascular development like for many other matricellular proteins including the integrin $\alpha_v\beta_3$ ligand osteopontin (30). In comparison, genetic ablation of integrin $\alpha_v$ is demonstrated to be lethal (40) and integrin $\beta_3$ deficiency resulted in prolonged bleeding and decreased fetal survival (41) showing the roles of the integrins in a multitude of processes and in various cell types.

Mfap4−/− mice underwent ligation of the left carotid artery in order to stop the blood flow and thereby causing the vessel to shrink in the luminal area due to the neointima formation and additional arterial remodeling (35). During the next 14 days, the EEL of the ligated vessels in mfap4−/− mice was reduced when compared to the unligated control vessels, without prominent acquisition of intimal mass. Intravascular ultrasound has previously confirmed the presence of both outward and constricting remodeling after angioplasty suggesting that an increase in the total EEL confined area is adaptive, whereas a decrease in the EEL area contributes to restenosis with occlusion of the lumen (42). As the mfap4−/− mice did not appear with prominent outward arterial remodeling, neither 14 nor 28 days after ligation, the delayed neointima formation ultimately resulted in a narrowing of the lumen 28 days after ligation. The effects appeared to be intrinsic consequences of the mfap4−/− phenotype and were detectable between mouse strains with two different genetic backgrounds (C57BL/6N and BALB/c). Reduced carotid neointima formation is previously observed in integrin $\beta_3$ deficiency (43) and with experiments performed using gene-deficiency for the integrin $\alpha_v\beta_3$ ligand vitronectin (44) or osteopontin inhibition experiments (45) where the gene deficiency appeared protective.

MFAP4 overexpression was recently demonstrated to preserve MMP (collagenase degrading MMP1 and elastolytic MMP12) activity after photodamaging of skin, and was suggested to affect the synthesis of these MMPs (34). MMP9 deficiency is demonstrated to reduce the VSMC migration and neointima formation in both endovascular denudation and carotid ligation experiments (46, 47). A vein-graft model has further demonstrated that the expansive vessel remodelling may be induced in MMP9 deficient mice due to compensatory upregulation of MMP2 (48). The inventors' observations on MMP9 expression indicated that MFAP4 deficiency reduces the synthesis of this enzyme. The transient and early reduction of the MMP9 transcription was not associated to outer vessel diameter expansion in the present studies, which rather showed constrictive remodeling with MFAP4 deficiency. These data suggests that unrecognized extracellular proteases in addition to MMP9 may be reduced by MFAP4 deficiency.

As known for integrin $\alpha_v\beta_3$-blocking antibodies (17) and other integrin $\alpha_v\beta_3$ antagonists (45) the MFAP4 blocking antibodies may be anticipated to target vasculoproliferative processes including VSMC driven restenosis and neovascularization. One putative advantage with MFAP4 blocking antibodies could be the selective inhibition of cellular integrins engaged in complexes with MFAP4, and the possible reduction of side effects from the integrin inhibition. Moreover, prophylactic anti-MFAP4 treatment could be initiated prior to an expected vascular damage due to the constitutive presence of MFAP4 in the vessels. However, such treatment may require relatively high amounts of antibody, unless applied topically. Moreover, although concern has existed regarding the safety of long-term systemic administration of integrin $\alpha_v\beta_3$ antagonists, including inhibition of wound healing and promotion of paradoxical cancerous activity (49) recent evidence has lessened this concern. Integrin $\alpha_v\beta_3$ antagonism appears with an acceptable level of adverse effects (50-52), and sustained systemic exposure with integrin $\alpha_v\beta_3$- or $\alpha_v\beta_5$-blocking antibodies did not inhibit wound healing in monkeys and humans (53, 54).

In summary, the results of this study show that MFAP4 plays a surprisingly multifacetted role in the vascular stenotic responses by promoting protective outward vessel remodeling but also the cellular growth and migration leading to hyperplasia. MFAP4 is constitutively expressed and thus has the potential to serve as prophylactic terapeutical target for inhibition of VSMC growth and migration. Additional obtained results show that absence of MFAP4 attenuates OVA-induced allergic airway disease. It indicates that MFAP4 may serve as a therapeutic target in the treatment of allergic asthma.

Production and Purification of Wild-Type rMFAP4 and RGD Mutants

Wild-type rMFAP4 and different genetically modified versions of the protein was performed as previously described (7).

Production of Anti-MFAP4 Monoclonal Antibodies

C57BL/6/N MFAP4 deficient mice were immunized for the production of monoclonal antibodies (HG HYB 7-5, 7-14, and 7-18) against rMFAP4.

Immunohistochemical Analysis

Freeze sections from a human vein with intimal hyperplasia was obtained from the Vascular Research Unit, Viborg Hospital. Formalin fixed normal human tissue was obtained from the tissue bank at the Department of Pathology, Odense University Hospital (Odense, Denmark). The local ethical committee in Odense approved the use of the human tissue sections (Ref. No. VF20050070). Mouse tissue was obtained from mfap4−/− or mfap4+/+ mice. Utilised antibodies included; anti-MFAP4 (HG-HYB 7-14), fluorescein isothiocyanate (FITC)-anti-MFAP4 (HG-HYB 7-14), anti-α-SMA (Dako #M0851), FITC-anti-α-SMA (Sigma, clone 1A4), anti-integrin $\alpha_v\beta_3$ (Santa Cruz #SC-7312), anti-human CD45 (Roche #760-4279), anti-mouse CD45 (BD pharmingen, clone 30-F11), anti-Ki-67 (Dako, clone MIB-1), anti-caspase-3 (Cell Signaling #9664), and anti-FITC antibody (P5100, Dako).

Ligand Binding Studies

Insoluble type I collagen from bovine Achilles tendon and insoluble elastin from bovine aorta were supplied by Sigma (St. Louis, Mo., USA) and Elastin Products Company, Inc. (Owensville, Mo., USA), respectively. Five milligram of collagen or elastin was hydrated overnight in 10 mM tris buffered saline (TBS) 0.05% (w/w) TWEEN 20, and 5 mM $CaCl_2$ (TBS/Tw-$Ca^{2+}$) or 10 mM Ethylenediaminetetraacetic acid (EDTA) (TBS/Tw-EDTA) at 4° C. and mixed with rMFAP4 in TBS/Tw-$Ca^{2+}$ or TBS/Tw-EDTA. After incubation at room temperature for 1 h, the water phase was recovered by centrifugation and analyzed by ELISA.

Detection of MFAP4 by ELISA

Sandwich ELISA assays were performed in 96-well Maxisorb Microplates (Nunc) essentially as described in Molleken et al. 2009 (32).

Statistical Methods

Statistical significance between groups in in vitro and in vivo experiments was assessed by one-way or (paired or unpaired) two-way ANOVA with Bonferroni adjusted t-tests when relevant. Data were analyzed using GraphPad Prism 5. $P<0.05$ was considered statistically significant.

HAoSMC Cultures

Cells were grown at 37° C. in 5% $CO_2$ humidified incubator (Hera cell, Heraeus). fHAoSMC's or adult cells (Cell application, inc.) derived from normal human tunica intima and media of either fetal or adult aorta, were cultured in a smooth muscle cell growth medium (Cell application, inc), or when allowed to differentiate in a smooth muscle cell differentiating medium (Cell application, inc.). Cells were used in passages 3-7.

Immunofluorescence Microscopy

Fixed and permeabilized cells were stained for 1 h at room temperature using 10 µg/ml FITC-anti-MFAP4 in phosphate buffered saline (PBS)/BSA containing 0.2% saponin (w/w).

Cell Adhesion Assay

Black 96-well Maxisorp FluoroNunc™ microtiter plates (Nunc) were basically coated as above. In blocking experiments well were further incubated with 20 µg/mL of MFAP4 blocking antibodies HG-HYB 7-5, 7-14 or 7-18 or fHAoSMCs were pre-incubated with either 25-100 µg/mL synthetic GRGDS or SDGRG peptides (Sigma-Aldrich) or 10 µg/mL anti-integrin antibodies; anti-integrin $\alpha_V$, monoclonal mouse anti-human antibody clone L230 (Alexis Biochemicals); anti-integrin $\beta_1$, monoclonal mouse anti-human antibody clone P4C10 (Millipore); anti-integrin $\alpha_V/\beta_5$, monoclonal mouse anti-human antibody clone P1F6 (Santa Cruz Biotechnologies); anti-integrin $\alpha_V/\beta_3$, monoclonal mouse anti-human antibody clone LM609 (Millipore); monoclonal mouse anti-fibrinogen C domain-containing protein 1 (anti-FIBCD1) antibody clone 12-5 (control antibody produced in-house (55)). A Vybrant™ cell adhesion assay kit (Molecular Probes, Invitrogen) was used.

Cell Migration Assay

The migration assay was performed using the Oris™ Migration Assembly Kit (Platypus Technologies Madison, Wis.) with coating as above. FHAoSMCs were serum-starved before the addition of 0.5% (w/w) fetal calf serum and 5 ng/ml PDGF-BB allowing cell migration. Some well were incubated with anti-MFAP4 antibody clones. Migrated cells were detected using 4',6-diamidino-2-phenylindole (DAPI) solution (Invitrogen).

Cell Proliferation Assay

FHAoSMCs were serum starved before seeding onto immobilized rMFAP4 or fibronectin. Blocking experiments were performed by incubating the protein coated wells with 20 µg/mL anti-MFAP4 antibodies, or by preincubating suspended fHAoSMCs with anti-integrin antibody in the presence of 0.3% (w/w) fetal calf serum ±5 ng/mL recombinant human PDGF-BB. The number of viable cells was following determined using an MTT-assay.

SDS-PAGE and Western Blotting

SDS-PAGE and Western Blotting were performed using standard methods. Primary antibodies included; anti-$\alpha_V$ (CD51), monoclonal mouse IgG clone 21 (BD Biosciences); anti-$\beta_1$, monoclonal mouse IgG clone BV7 (abcam); anti-$\beta_3$, polyclonal goat IgG clone C-20 (Santa Cruz Biotechnology); anti-$\beta_5$, polyclonal rabbit IgG clone H-96 (Santa Cruz Biotechnology); anti-MFAP4, monoclonal HG-HYB 7-5; Anti-Glyceraldehyde-3-phosphate dehydrogenase (GAPDH), monoclonal mouse IgG clone 6C5 (Santa Cruz Biotechnology); anti-$\alpha$-SMA, monoclonal mouse IgG clone 1A4 (Sigma-Aldrich). Secondary antibodies included: horseraddish peroxidase (HRP)-labelled donkey anti-goat immunoglobulin (Santa Cruz Biotechnology), goat anti-rabbit immunoglobulin HRP-labelled (Dako), and rabbit anti-mouse immunoglobulin HRP-labelled (Dako).

FACS Analysis

Pelleted FHAoSMCs were resuspended with relevant primary anti-integrin antibodies described under "cell adhesion assay" or isotype matched anti-chicken ovalbumin (The State Serum Institute, Copenhagen) and polyclonal anti-mouse FITC-conjugated goat $F(ab')_2$ (Dako) as secondary antibody. Cells were analyzed using a Becton Dickinson (BD) Flow Cytometry FACScan™ (BD Biosciences) and BD Cell Quest™ Software (BD Biosciences).

Generation of MFAP4 Deficient Mice

A targeting vector was constructed to delete genomic regions encompassing the core promoter region, exons 1, 2 and a part of 3 for elimination of the MFAP4 transcription. A neomycin expression cassette was ligated into the targeting vector. CJ7 embryonic stem cells were electroporated with the linerized targeting vector. Chimeric mice with the targeted ES cell clones were developed and their descendants were backcrossed to C57Bl/6N and BALB/c (Charles River Laboratories International) for 11 generations and maintained as heterozygotes.

Carotid Artery Ligation Model

All mouse experimens were performed under a license obtained from The National Animal Experiments Inspectorate who also approved the study (ref. no. 2012-15-2934-00095). The arterial ligation model was essentially performed as described in Kumar and Lindner 1997 (35).

OVA-Induced Allergic Asthma Model

MFAP4 WT and KO mice were sensitized intraperitoneally with 20 ug OVA with 2 mg alum in 200 ul PBS on days 0 and 7. One week later mice were challenged intranasally with 20 ug OVA in 50 ul PBS during three consecutive days. 2 mg alum in PBS and PBS only served as controls for sensitization and challenge, respectively.

Bronchoalveolar Lavage

Anaesthetized animals were sacrificed 24 h after final challenge. The trachea was cannulated, and BAL was collected by washing the airway lumen four times with 0.5 ml PBS. Cells were cytospun at 200 g for 5 min. and subsequently stained with Hemacolor (Merck). Differential cell count was performed based on morphological criteria.

Lung Histology

Lungs were excised, inflated with 10% formalin and processed for histology. The level of parenchymal inflammation was assessed on slides stained with hematoxylin-eosin (H-E). Periodic acid-Schiff (PAS) staining was used to visualise mucus-producing goblet cells. Epithelial thickness was measured using ImageJ software. All analyses were performed in a blinded manner.

RT-qPCR

Total RNA was from ligated and unligated carotid arteries was processed using standard methods Relative expression was assessed using TaqMan® assays (Applied Biosystems by Life Technologies); mfap4: Mm00840681_m1; integrin $\beta_3$ (Itgb3): Mm004439980_m1; MMP9: Mm00442991_m1; TATA-binding protein (TBP) (endogenous control1): Mm00446973_m1; GAPDH (endogenous control2): Mm99999915_g1.

Microfibrillar Associated Protein 4 (MFAP4) as Modulator of the ASM-Dependent Asthmatic Remodelling.

The present inventors originally identified MFAP4 from lung washings [56] and subsequently localized the protein to various elastic tissues [57]. MFAP4 is synthesized by and secreted from smooth muscle cells and is localized on the elastic fibres in the interalveolar septum and in elastic lamina of pulmonary arteries of chronically inflamed lung tissue [58]. MFAP4 is a polymeric protein formed from 66 kDa protein dimers [56]. The C-terminal fibrinogen-like domain is responsible for elastin and collagen binding, whereas the N-terminal region includes an RGD sequence responsible for interactions with integrin receptors [62]. Proteome analysis of fibrotic liver tissue coupled with our measurements of serum MFAP4 revealed that MFAP4 serves as systemic marker for the fibrotic stages [63].

The inventors have produced MFAP4-deficient mice (mfap4−/−). High expression in the vascular compartment and intense staining for MFAP4 in the vessel wall elastic fibres [64] has prompted us to investigate vascular remodelling in mfap4−/− mice. Using the carotid ligation model we have clear evidence that smooth muscle cell neointima formation and vascular smooth muscle cell (VSMC) proliferation are substantially reduced in the gene deficient mice. The present inventors could explain the observation through the interaction between MFAP4 and integrins and have further demonstrated that VSMC migration and proliferation is significantly increased by MFAP4 and may be reversed using our in house produced MFAP4-blocking antibodies.

The putative role of MFAP4 in asthma is unknown. However, our characterization of MFAP4 as an integrin ligand, mediator of smooth muscle cell proliferation, adhesion and migration and the high pulmonary expression of MFAP4 clearly suggest us to investigate its potential role in the asthma pathogenesis.

Figure 9:
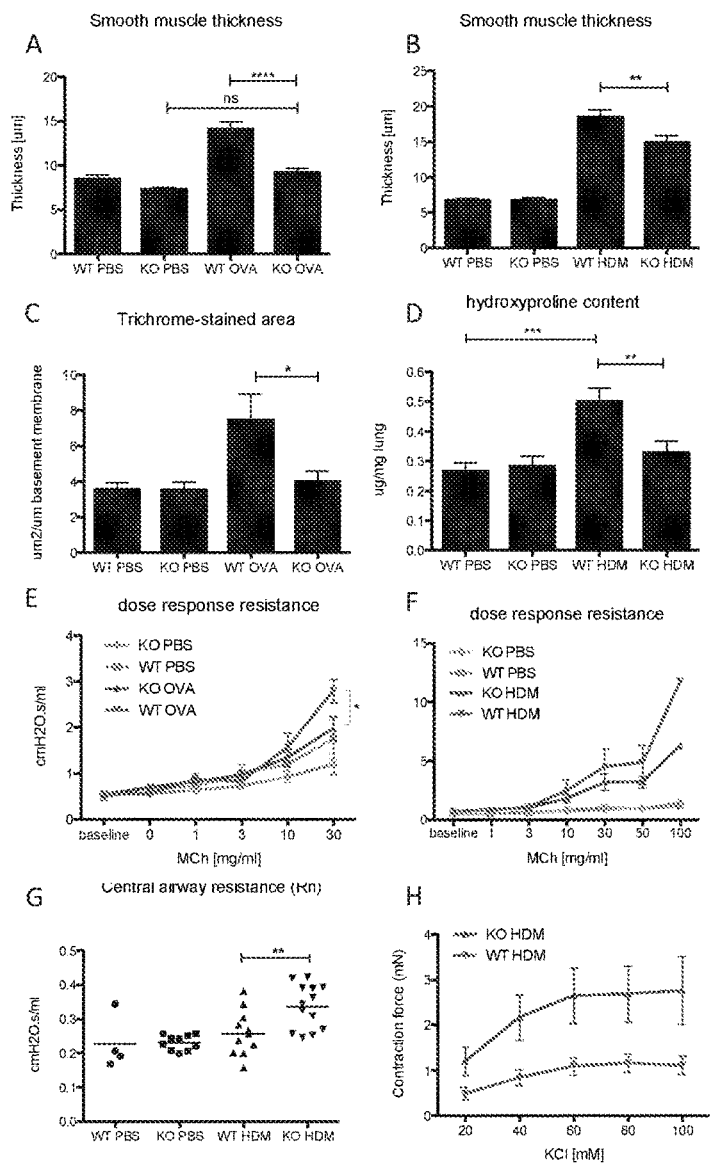
FIG. 9 shows MFAP4-deficient mice that are partially protected from airway remodelling and AHR, but exhibit increased tracheal contractility. Morphometric analysis of smooth muscle/myofibroblast layer thickness in OVA (A) or HDM-treated mice (B) as evaluated by alpha-smooth muscle actin immunostaining. Quantification of the fibrotic response was performed by morphometric analysis of peri-bronchial collagen deposition (C) or measuring hydroxyproline content in lung homogenates (D). (E-F) AHR in response to nebulized methacholine challenge is dampened in MFAP4-deficient animals. (G) Central airway resistance measurement as a surrogate for tracheal stiffness. (H) KCl-induced tracheal ring contractility measurements. *p<0.05, p<0.01, *p<0.001 as indicated by Student's t-test or ANOVA.
Figure 10:
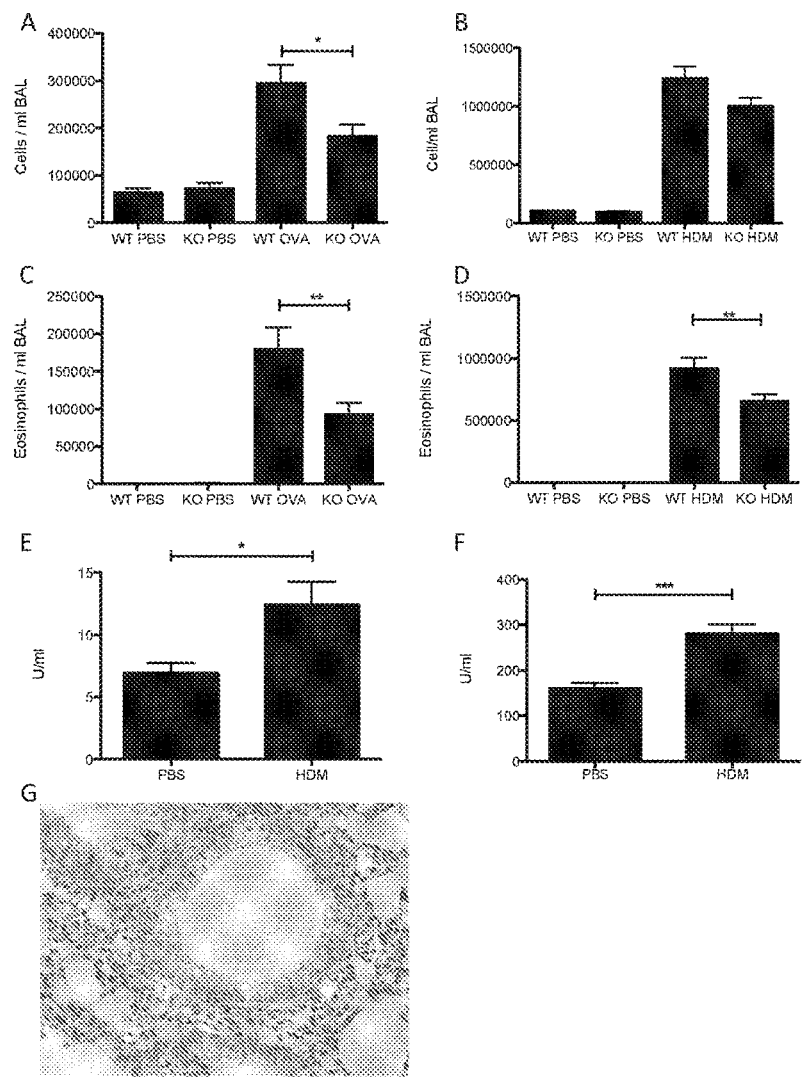
FIG. 10 shows cellular infiltration in BAL after allergen treatment is lowered in MFAP4-deficient mice. Quantification of total BAL cells (A, B) and eosinophils (C, D) from both OVA (A, C) and HDM models (B, D) is shown. Chronic HDM exposure results in increased soluble MFAP4 content in BAL (E) and serum (F). MFAP4 is localized to the bronchial basal membrane by immunohistochemistry using monoclonal antibodies. *p<0.05, p<0.01, *p<0.001 as indicated by Student's t-test or ANOVA.

The inventors divided female Balb/c mice into 2*4 groups 1) mfap4+/+ saline, 2) mfap4+/+ house dust mite extract inhalation for seven weeks or ovalbumin sensitization and challenge for three weeks (HDM or OVA), 3) mfap4−/− saline, and 4) mfap4−/− HDM or OVA. Morphometric analysis of the peribronchiolar smooth muscle layer showed increased ASM layer thickness in mfap4+/+ relative to mfap4−/− (FIG. 9A-B). Likewise, the collagen (Trichrome)-stained area per μm of basal membrane or the total hydroxyproline content was increased in the mfap4+/+ mice (FIG. 9C-D). The central airway resistance was increased with allergic asthma but to a significantly higher degree in mfap4−/− relative to mfap4+/+ and there was likewise a tendency for increased metacholine induced airway hyperreactivity (FIG. 9E-G). Moreover, the KCl-induced contraction force in the isolated tracheas measured after allergen treatment was increased in MFAP4-deficient mice (FIG. 9H). The bronchoalveolar lavage (BAL) infiltration was significantly higher in OVA-treated mfap4+/+ mice relative to mfap4−/− mice, and the same tendency was found in HDM-treated animals (FIG. 10A-B). Infiltrating cells in lung tissue as well as in BAL consisted primarily of eosinophils, whose numbers where significantly increased in mfap4+/+ BAL relative to mfap4−/− (FIG. 10C-D). MFAP4 levels measured by ELISA as previously described [64] in BAL and serum showed that allergic asthma results in increased MFAP4 levels in these body fluids (FIG. 10E-F). MFAP4 was located to the basal layer of the bronchi (FIG. 10G) and did not appear with visually detectable diseased induced changes in expression at that location.

The inventors have contemplated a study based on Perkins et al., 2011 [66] and their own experience with similar assays using vascular smooth muscle cells. The following four prophetic experiments will detail the study.

MFAP4-Dependent Integrin Modulation of ASM Phenotype In Vitro and Ex Vivo:

Primary human bronchial smooth muscle cells will be used as well as smooth muscle cells isolated from wildtype and mfap4−/− mouse tracheas[66]. The present inventors will conclusively identify the specific integrin/s interacting with MFAP4 in the ASM. Affinity purification of MFAP4 ligands on MFAP4 coupled to Sepharose 4B will be performed using an array of relevant monoclonal anti-integrin antibodies. Moreover, the present inventors will immunoprecipitate ASM cell lysates with MFAP4 antibodies and analyse by Western Blotting with the relevant integrin antibodies.

The Role of MFAP4 and MFAP4-Blocking Antibodies in ASM Proliferation and Migration:

The present inventors will test MFAP4-dependent modulation of ASM adhesion, proliferation and migration. To test if MFAP4 treatment leads to conversion of quiescent ASM into a more adhesive or proliferative state, recombinant MFAP4 will be coated onto the tissue culture surface and/or platelet derived growth factor (PDGF) will be added into the culture medium and the proliferating fraction of cells will be estimated by colorimetric assay (MTT assay). The migratory response will be examined using similar cell culture conditions in a two-dimensional migration assay (Oris Cell Migration Assembly Kit, Platypus Technologies). The integrin dependency in all assays will be tested using relevant integrin blocking antibodies and anti-MFAP4 blocking antibodies.

The Role for MFAP4 in Eosinophil Chemotaxis:

To test potential MFAP4-dependent eosinophil migration, the present inventors will isolate eosinophils from mfap4−/− (control) and mfap4+/+ mice sensitized and challenged with allergen from the lungs. The chemotactic response to increased concentrations of MFAP4 will be checked by Transwell assay.

Moreover, primary human bronchial smooth muscle cells will be grown on MFAP4-coated plates or in the presence of soluble MFAP4, and the production of eosinophil chemoattractants CCL11, CCL24 and CCL5 will be analysed by qPCR and/or ELISA.

The Role of MFAP4 in Airway Contraction Force Development:

The present inventors will measure isometric tension in tracheal rings from mfap4−/− (control) and mfap4+/+ animals in the presence of MFAP4-blocking antibodies. Tracheas will be isolated from animals and single open-ring, epithelium-denuded preparations will be mounted in organ baths. The tissue will be preincubated with antibodies and precontracted with KCl and following maximal relaxation will be established by the addition of isoproterenol. Stepwise increasing concentrations of KCl or methacholine will be included to measure maximal tension. According to the outcome of analysis the experiment will be repeated on isolated bronchi from freshly resected cancer patient lung tissue in collaborative effort with thorax surgeon Peter Licht, Odense University Hospital.

REFERENCES

1. Ross R. Cell biology of atherosclerosis. Annu Rev Physiol. 1995; 57:791-804. Epub 1995 Jan. 1.
2. Casscells W. Migration of smooth muscle and endothelial cells. Critical events in restenosis. Circulation. 1992; 86(3):723-9. Epub 1992 Sep. 1.

3. Libby P, Tanaka H. The molecular bases of restenosis. Progress in cardiovascular diseases. 1997; 40(2):97-106. Epub 1997 Nov. 5.
4. Owens G K, Kumar M S, Wamhoff B R. Molecular regulation of vascular smooth muscle cell differentiation in development and disease. Physiol Rev. 2004; 84(3): 767-801. Epub 2004 Jul. 23.
5. Gomez D, Owens G K. Smooth muscle cell phenotypic switching in atherosclerosis. Cardiovasc Res. 2012. Epub 2012 Mar. 13.
6. Zhao Z, Lee C C, Jiralerspong S, Juyal R C, Lu F, Baldini A, et al. The gene for a human microfibril-associated glycoprotein is commonly deleted in Smith-Magenis syndrome patients. Hum Mol Genet. 1995; 4(4):589-97. Epub 1995 Apr. 1.
7. Schlosser A, Thomsen T, Shipley J M, Hein P W, Brasch F, Tornoe I, et al. Microfibril-associated protein 4 binds to surfactant protein A (SP-A) and colocalizes with SP-A in the extracellular matrix of the lung. Scandinavian journal of immunology. 2006; 64(2):104-16. Epub 2006 Jul. 27.
8. Lausen M, Lynch N, Schlosser A, Tornoe I, Saekmose S G, Teisner B, et al. Microfibril-associated protein 4 is present in lung washings and binds to the collagen region of lung surfactant protein D. The Journal of biological chemistry. 1999; 274(45):32234-40.
9. Thomsen T, Schlosser A, Holmskov U, Sorensen G L. Ficolins and FIBCD1: Soluble and membrane bound pattern recognition molecules with acetyl group selectivity. Molecular immunology. 2010. Epub 2010 Nov. 13.
10. Kobayashi R, Tashima Y, Masuda H, Shozawa T, Numata Y, Miyauchi K, et al. Isolation and characterization of a new 36-kDa microfibril-associated glycoprotein from porcine aorta. The Journal of biological chemistry. 1989; 264(29):17437-44. Epub 1989 Oct. 15.
11. Toyoshima T, Ishida T, Nishi N, Kobayashi R, Nakamura T, Itano T. Differential gene expression of 36-kDa microfibril-associated glycoprotein (MAGP-36/MFAP4) in rat organs. Cell Tissue Res. 2008; 332(2):271-8. Epub 2008 Mar. 7.
12. Toyoshima T, Nishi N, Kusama H, Kobayashi R, Itano T. 36-kDa microfibril-associated glycoprotein (MAGP-36) is an elastin-binding protein increased in chick aortae during development and growth. Exp Cell Res. 2005; 307(1):224-30. Epub 2005 Jun. 1.
13. Toyoshima T, Yamashita K, Furuichi H, Shishibori T, Itano T, Kobayashi R. Ultrastructural distribution of 36-kD microfibril-associated glycoprotein (MAGP-36) in human and bovine tissues. J Histochem Cytochem. 1999; 47(8):1049-56. Epub 1999 Jul. 29.
14. Kobayashi R, Mizutani A, Hidaka H. Isolation and characterization of a 36-kDa microfibril-associated glycoprotein by the newly synthesized isoquinolinesulfonamide affinity chromatography. Biochem Biophys Res Commun. 1994; 198(3):1262-6. Epub 1994 Feb. 15.
15. Hirano E, Fujimoto N, Tajima S, Akiyama M, Ishibashi A, Kobayashi R, et al. Expression of 36-kDa microfibril-associated glycoprotein (MAGP-36) in human keratinocytes and its localization in skin. Journal of dermatological science. 2002; 28(1):60-7. Epub 2002 Mar. 28.
16. Sajid M, Stouffer G A. The role of alpha(v)beta3 integrins in vascular healing. Thrombosis and haemostasis. 2002; 87(2):187-93. Epub 2002 Feb. 23.
17. Kokubo T, Uchida H, Choi E T. Integrin alpha(v)beta(3) as a target in the prevention of neointimal hyperplasia. J Vasc Surg. 2007; 45 Suppl A:A33-8. Epub 2007 Aug. 8.
18. Panda D, Kundu G C, Lee B I, Peri A, Fohl D, Chackalaparampil I, et al. Potential roles of osteopontin and alphaVbeta3 integrin in the development of coronary artery restenosis after angioplasty. Proceedings of the National Academy of Sciences of the United States of America. 1997; 94(17):9308-13. Epub 1997 Aug. 19.
19. Dufourcq P, Louis H, Moreau C, Daret D, Boisseau M R, Lamaziere J M, et al. Vitronectin expression and interaction with receptors in smooth muscle cells from human atheromatous plaque. Arterioscler Thromb Vasc Biol. 1998; 18(2):168-76. Epub 1998 Mar. 4.
20. Li G, Jin R, Norris R A, Zhang L, Yu S, Wu F, et al. Periostin mediates vascular smooth muscle cell migration through the integrins alphavbeta3 and alphavbeta5 and focal adhesion kinase (FAK) pathway. Atherosclerosis. 2010; 208(2):358-65. Epub 2009 Aug. 22.
21. Nakamura T, Lozano P R, Ikeda Y, Iwanaga Y, Hinek A, Minamisawa S, et al. Fibulin-5/DANCE is essential for elastogenesis in vivo. Nature. 2002; 415(6868):171-5. Epub 2002 Jan. 24.
22. Ishigaki T, Imanaka-Yoshida K, Shimojo N, Matsushima S, Taki W, Yoshida T. Tenascin-C enhances crosstalk signaling of integrin alphavbeta3/PDGFR-beta complex by SRC recruitment promoting PDGF-induced proliferation and migration in smooth muscle cells. Journal of cellular physiology. 2011; 226(10):2617-24. Epub 2011 Jul. 28.
23. Maile L A, Allen L B, Hanzaker C F, Gollahon K A, Dunbar P, Clemmons D R. Glucose regulation of thrombospondin and its role in the modulation of smooth muscle cell proliferation. Experimental diabetes research. 2010; 2010. Epub 2010 Aug. 7.
24. Liaw L, Skinner M P, Raines E W, Ross R, Cheresh D A, Schwartz S M, et al. The adhesive and migratory effects of osteopontin are mediated via distinct cell surface integrins. Role of alpha v beta 3 in smooth muscle cell migration to osteopontin in vitro. The Journal of clinical investigation. 1995; 95(2):713-24. Epub 1995 Feb. 1.
25. van der Flier A, Sonnenberg A. Function and interactions of integrins. Cell Tissue Res. 2001; 305(3):285-98. Epub 2001 Sep. 27.
26. Hoshiga M, Alpers C E, Smith L L, Giachelli C M, Schwartz S M. Alpha-v beta-3 integrin expression in normal and atherosclerotic artery. Circ Res. 1995; 77(6): 1129-35. Epub 1995 Dec. 1.
27. Corjay M H, Diamond S M, Schlingmann K L, Gibbs S K, Stoltenborg J K, Racanelli A L. alphavbeta3, alphavbeta5, and osteopontin are coordinately upregulated at early time points in a rabbit model of neointima formation. Journal of cellular biochemistry. 1999; 75(3):492-504. Epub 1999 Oct. 28.
28. Srivatsa S S, Fitzpatrick L A, Tsao P W, Reilly T M, Holmes D R, Jr., Schwartz R S, et al. Selective alpha v beta 3 integrin blockade potently limits neointimal hyperplasia and lumen stenosis following deep coronary arterial stent injury: evidence for the functional importance of integrin alpha v beta 3 and osteopontin expression during neointima formation. Cardiovasc Res. 1997; 36(3):408-28. Epub 1998 Apr. 16.
29. Preissner K T, Reuning U. Vitronectin in vascular context: facets of a multitalented matricellular protein. Seminars in thrombosis and hemostasis. 2011; 37(4):408-24. Epub 2011 Aug. 2.
30. Frangogiannis N G. Matricellular proteins in cardiac adaptation and disease. Physiol Rev. 2012; 92(2):635-88. Epub 2012 Apr. 27.
31. Sage E H. Regulation of interactions between cells and extracellular matrix: a command performance on several 32. Molleken C, Sitek B, Henkel C, Poschmann G, Sipos B, Wiese S, et al. Detection of novel biomarkers of liver cirrhosis by proteomic analysis. Hepatology. 2009; 49(4): 1257-66. Epub 2009 Jan. 30.
33. Abdul-Salam V B, Wharton J, Cupitt J, Berryman M, Edwards R J, Wilkins M R. Proteomic analysis of lung tissues from patients with pulmonary arterial hypertension. Circulation. 2010; 122(20):2058-67. Epub 2010 Nov. 3.
34. Kasamatsu S, Hachiya A, Fujimura T, Sriwiyanont P, Haketa K, Visscher M O, et al. Essential role of microfibrillar-associated protein 4 in human cutaneous homeostasis and in its photoprotection. Scientific Reports. 2011; 1(164):1-10.
35. Kumar A, Lindner V. Remodeling with neointima formation in the mouse carotid artery after cessation of blood flow. Arterioscler Thromb Vasc Biol. 1997; 17(10):2238-44. Epub 1997 Nov. 14.
36. Fitzpatrick L A, Severson A, Edwards W D, Ingram R T. Diffuse calcification in human coronary arteries. Association of osteopontin with atherosclerosis. The Journal of clinical investigation. 1994; 94(4):1597-604. Epub 1994 Oct. 1.
37. Myers D L, Harmon K J, Lindner V, Liaw L. Alterations of arterial physiology in osteopontin-null mice. Arterioscler Thromb Vasc Biol. 2003; 23(6):1021-8. Epub 2003 Apr. 26.
38. Baron J H, Moiseeva E P, de Bono D P, Abrams K R, Gershlick A H. Inhibition of vascular smooth muscle cell adhesion and migration by c7E3 Fab (abciximab): a possible mechanism for influencing restenosis. Cardiovasc Res. 2000; 48(3):464-72. Epub 2000 Nov. 25.
39. Varadarajulu J, Laser M, Hupp M, Wu R, Hauck C R. Targeting of alpha(v) integrins interferes with FAK activation and smooth muscle cell migration and invasion. Biochem Biophys Res Commun. 2005; 331(2):404-12. Epub 2005 Apr. 27.
40. Bader B L, Rayburn H, Crowley D, Hynes R O. Extensive vasculogenesis, angiogenesis, and organogenesis precede lethality in mice lacking all alpha v integrins. Cell. 1998; 95(4):507-19. Epub 1998 Nov. 25.
41. Hodivala-Dilke K M, McHugh K P, Tsakiris D A, Rayburn H, Crowley D, Ullman-Cullere M, et al. Beta3-integrin-deficient mice are a model for Glanzmann thrombasthenia showing placental defects and reduced survival. The Journal of clinical investigation. 1999; 103(2):229-38. Epub 1999 Jan. 23.
42. Mintz G S, Popma J J, Pichard A D, Kent K M, Satler L F, Wong C, et al. Arterial remodeling after coronary angioplasty: a serial intravascular ultrasound study. Circulation. 1996; 94(1):35-43. Epub 1996 Jul. 1.
43. Choi E T, Khan M F, Leidenfrost J E, Collins E T, Boc K P, Villa B R, et al. Beta3-integrin mediates smooth muscle cell accumulation in neointima after carotid ligation in mice. Circulation. 2004; 109(12):1564-9. Epub 2004 Mar. 10.
44. Peng L, Bhatia N, Parker A C, Zhu Y, Fay W P. Endogenous vitronectin and plasminogen activator inhibitor-1 promote neointima formation in murine carotid arteries. Arterioscler Thromb Vasc Biol. 2002; 22(6):934-9. Epub 2002 Jun. 18.
45. Han M, Wen J K, Zheng B, Liu Z, Chen Y. Blockade of integrin beta3-FAK signaling pathway activated by osteopontin inhibits neointimal formation after balloon injury. Cardiovascular pathology: the official journal of the Society for Cardiovascular Pathology. 2007; 16(5):283-90. Epub 2007 Sep. 18.
46. Johnson C, Galis Z S. Matrix metalloproteinase-2 and -9 differentially regulate smooth muscle cell migration and cell-mediated collagen organization. Arterioscler Thromb Vasc Biol. 2004; 24(1):54-60. Epub 2003 Oct. 11.
47. Cho A, Reidy M A. Matrix metalloproteinase-9 is necessary for the regulation of smooth muscle cell replication and migration after arterial injury. Circ Res. 2002; 91(9):845-51. Epub 2002 Nov. 2.
48. Thomas A C, Newby A C. Effect of matrix metalloproteinase-9 knockout on vein graft remodelling in mice. J Vasc Res. 2010; 47(4):299-308. Epub 2009 Dec. 18.
49. Carter A. Integrins as target: first phase III trial launches, but questions remain. Journal of the National Cancer Institute. 2010; 102(10):675-7. Epub 2010 May 13.
50. Murphy M G, Cerchio K, Stoch S A, Gottesdiener K, Wu M, Recker R. Effect of L-000845704, an alphaVbeta3 integrin antagonist, on markers of bone turnover and bone mineral density in postmenopausal osteoporotic women. The Journal of clinical endocrinology and metabolism. 2005; 90(4):2022-8. Epub 2005 Feb. 3.
51. Hersey P, Sosman J, O'Day S, Richards J, Bedikian A, Gonzalez R, et al. A randomized phase 2 study of etaracizumab, a monoclonal antibody against integrin alpha (v)beta(3), + or − dacarbazine in patients with stage IV metastatic melanoma. Cancer. 2010; 116(6):1526-34. Epub 2010 Jan. 29.
52. Rosenthal M A, Davidson P, Rolland F, Campone M, Xue L, Han T H, et al. Evaluation of the safety, pharmacokinetics and treatment effects of an alpha(nu)beta(3) integrin inhibitor on bone turnover and disease activity in men with hormone-refractory prostate cancer and bone metastases. Asia-Pacific journal of clinical oncology. 2010; 6(1):42-8. Epub 2010 Apr. 20.
53. Martin P L, Jiao Q, Cornacoff J, Hall W, Saville B, Nemeth J A, et al. Absence of adverse effects in cynomolgus macaques treated with ONTO 95, a fully human anti-alphav integrin monoclonal antibody, despite widespread tissue binding. Clin Cancer Res. 2005; 11(19 Pt 1):6959-65. Epub 2005 Oct. 6.
54. Zhang D, Pier T, McNeel D G, Wilding G, Friedl A. Effects of a monoclonal anti-alphavbeta3 integrin antibody on blood vessels—a pharmacodynamic study. Investigational new drugs. 2007; 25(1):49-55. Epub 2006 Sep. 27.
55. Schlosser A, Thomsen T, Moeller J B, Nielsen O, Tornoe I, Mollenhauer J, et al. Characterization of FIBCD1 as an acetyl group-binding receptor that binds chitin. J Immunol. 2009; 183(6):3800-9. Epub 2009 Aug. 28
56. ZHAO Z. et al.: "The gene for a human microfibril-associated glycoprotein is commonly deleted in Smith-Magenis syndrome patients", HUMAN MOLECULAR GENETICS, Vol. 4, No. 4, 1995, pages 589-597
57. VASSILEV T. L. et al.: "Inhibition of Cell Adhesion by Antibodies to Arg-Gly-Asp (RGD) in Normal Immunoglobulin for Therapeutic Use (Intravenous Immunoglobulin, IVIg)", BLOOD, Vol. 93, 1999, pages 3624-3631
58 KOKUBO T. et al.: "Integrin $\alpha v \beta 3$ as a Target in the Prevention of neointimal Hyperplasia", J VASC SURG., Vol. 45, No. 6S, 2007, pages 33-38
59. Lausen M, Lynch N, Schlosser A, Tornoe I, Saekmose S G, et al. (1999) Microfibril-associated protein 4 is present in lung washings and binds to the collagen region of lung surfactant protein D. J Biol Chem 274: 32234-32240

60. Toyoshima T, Ishida T, Nishi N, Kobayashi R, Nakamura T, et al. (2008) Differential gene expression of 36-kDa microfibril-associated glycoprotein (MAGP-36/MFAP4) in rat organs. Cell Tissue Res 332: 271-278.
61. Schlosser A (2004) Microfibril-associated protein 4 (MFAP4) and FReD-1. Two members of the fibrinogen domain superfamily. PHD Thesis: 1-64.
62. Toyoshima T, Nishi N, Kusama H, Kobayashi R, Itano T (2005) 36-kDa microfibril-associated glycoprotein (MAGP-36) is an elastin-binding protein increased in chick aortae during development and growth. Exp Cell Res 307: 224-230.
63. Molleken C, Sitek B, Henkel C, Poschmann G, Sipos B, et al. (2009) Detection of novel biomarkers of liver cirrhosis by proteomic analysis. Hepatology 49: 1257-1266.
64. Wulf-Johansson H, Lock Johansson S, Schlosser A, Trommelholt Holm A, Melholt Rasmussen L, et al. (2013) Localization of Microfibrillar-Associated Protein 4 (MFAP4) in Human Tissues: Clinical Evaluation of Serum MFAP4 and Its Association with Various Cardiovascular Conditions. PLoS One 8: e82243.
65. Saekmose S G, Schlosser A, Hoist R, Johansson S L, Wulf-Johansson H, et al. (2013) Enzyme-linked immunosorbent assay characterization of Basal variation and heritability of systemic microfibrillar-associated protein 4. PLoS One 8: e82383.
66. Perkins C, Yanase N, Smulian G, Gildea L, Orekov T, et al. (2011) Selective stimulation of IL-4 receptor on smooth muscle induces airway hyperresponsiveness in mice. J Exp Med 208: 853-867.

The invention claimed is:

1. An antibody which specifically blocks the integrin interacting motif in human microfibrillar-associated protein 4 (MFAP4) and, wherein the antibody is a preparation containing one or more monoclonal antibodies; said antibody having a light chain variable region comprising the amino acid sequence of SEQ ID NO 1, and a heavy chain variable region comprising the amino acid sequence of SEQ ID NO 3.

2. The antibody of claim 1 coupled to a detectable label or a substance having toxic or therapeutic activity.

3. The antibody of claim 1, wherein the antibody reduces the interaction of vascular smooth muscle cells with microfibrillar-associated protein 4.

4. The antibody of claim 1, wherein the antibody inhibits vascular smooth muscle cell migration and proliferation.

5. An in vitro method of inhibiting interaction of vascular smooth muscle cells with microfibrillar-associated protein 4, the method comprising:
   contacting the antibody of claim 1 with a population of vascular smooth muscle cells.

6. The method of claim 5, wherein the antibody of claim 1 is coupled to a detectable label or a substance having toxic or therapeutic activity.

7. An in vitro method of inhibiting vascular smooth muscle cell migration and proliferation, the method comprising:
   contacting the antibody of claim 1 with a population of vascular smooth muscle cells.

8. The method of claim 7, wherein the antibody of claim 1 is coupled to a detectable label or a substance having toxic or therapeutic activity.

\* \* \* \* \*

```
                          SEQUENCE LISTING

<160> NUMBER OF SEQ ID NOS: 32

<210> SEQ ID NO 1
<211> LENGTH: 108
<212> TYPE: PRT
<213> ORGANISM: Artificial Sequence
<220> FEATURE:
<223> OTHER INFORMATION: light chain variable regions

<400> SEQUENCE: 1

Asp Ile Val Met Thr Gln Ser Thr Ala Leu Met Ala Ala Ser Pro Gly
1               5                   10                  15

Glu Lys Val Thr Ile Thr Cys Ser Val Ser Ser Ile Ser Ser
            20                  25                  30

Asn Leu His Trp Tyr Gln Gln Lys Ser Glu Thr Ser Pro Lys Ser Trp
        35                  40                  45

Ile Tyr Gly Thr Ser Asn Leu Ala Ser Gly Val Pro Gly Arg Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Trp Ser Ser Tyr Pro
                85                  90                  95

Leu Thr Phe Gly Gly Gly Thr Lys Leu Glu Ile Lys
            100                 105

<210> SEQ ID NO 2
<211> LENGTH: 107
<212> TYPE: PRT
<213> ORGANISM: Artificial Sequence
<220> FEATURE:
<223> OTHER INFORMATION: light chain variable region

<400> SEQUENCE: 2

Asp Ile Val Leu Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Arg Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80
```

```
Glu Asp Phe Ala Met Tyr Tyr Cys Gln Gln His Asn Glu Tyr Pro Phe
                85                  90                  95

Thr Phe Gly Ala Gly Thr Lys Leu Glu Leu Lys
            100                 105

<210> SEQ ID NO 3
<211> LENGTH: 120
<212> TYPE: PRT
<213> ORGANISM: Artificial Sequence
<220> FEATURE:
<223> OTHER INFORMATION: heavy chain variable region

<400> SEQUENCE: 3

Glu Val Gln Leu Gln Gln Ser Gly Pro Glu Leu Val Lys Pro Gly Ala
1               5                   10                  15

Ser Val Lys Leu Ser Cys Lys Thr Ser Gly Tyr Thr Phe Thr Ser Tyr
            20                  25                  30

Asp Met Asn Trp Val Lys Gln Arg Pro Gly Gln Gly Leu Glu Trp Ile
        35                  40                  45

Gly Trp Ile Phe Pro Arg Asp Gly Ser Thr Lys Phe Asn Glu Lys Phe
    50                  55                  60

Lys Gly Lys Ala Thr Leu Thr Val Asp Thr Ser Ser Thr Thr Ala Tyr
65                  70                  75                  80

Met Glu Leu His Ser Leu Thr Ser Glu Asp Ser Ala Val Tyr Phe Cys
                85                  90                  95

Ala Arg Ala Glu Ile Phe Phe Asp Tyr Gly Phe Asp Tyr Trp Gly Gln
            100                 105                 110

Gly Thr Thr Leu Thr Val Ser Ser
        115                 120

<210> SEQ ID NO 4
<211> LENGTH: 123
<212> TYPE: PRT
<213> ORGANISM: Artificial Sequence
<220> FEATURE:
<223> OTHER INFORMATION: heavy chain variable region

<400> SEQUENCE: 4

Glu Val Lys Val Val Glu Ser Gly Gly Gly Leu Val Gln Pro Gly Gly
1               5                   10                  15

Ser Leu Arg Leu Ser Cys Ala Thr Ser Gly Phe Thr Phe Ser Asp Phe
            20                  25                  30

Tyr Met Glu Trp Val Arg Gln Pro Pro Gly Lys Arg Leu Glu Trp Ile
        35                  40                  45

Ala Ala Ser Arg Asn Lys Ala Asn Asp Tyr Thr Thr Glu Tyr Ser Ala
    50                  55                  60

Ser Val Lys Gly Arg Phe Ile Val Ser Arg Asp Thr Ser Gln Ser Ile
65                  70                  75                  80

Leu Tyr Leu Gln Leu Asn Ala Leu Arg Ala Glu Asp Thr Ala Ile Tyr
                85                  90                  95

Tyr Cys Ala Arg Asn Tyr Tyr Asp Ser Ser Tyr Trp Tyr Phe Asp Val
            100                 105                 110

Trp Gly Ala Gly Thr Thr Val Thr Val Ser Ser
        115                 120

<210> SEQ ID NO 5
<211> LENGTH: 320
<212> TYPE: DNA
<213> ORGANISM: Artificial Sequence
```

```
<220> FEATURE:
<223> OTHER INFORMATION: cDNA

<400> SEQUENCE: 5
gacattgtga tgacccagtc tacagcactc atggctgcat ctccagggga gaaggtcacc      60
atcacctgca gtgtcagctc aagtataagt tccagcaact tgcactggta ccagcagaag     120
tcagaaatcc cccaaatcct ggatttatgg cacatccaac ctggcttctg gagtccctgg     180
tcgcttcagt ggcagtggat ctgggacctc ttattctctc acaatcagca gcgtggaggc     240
tgaagatgct gccctattac tgtcaacagt ggagtagtta cccactgacg ttcggtggag     300
gcaccaagct ggaaatcaaa                                                  320

<210> SEQ ID NO 6
<211> LENGTH: 317
<212> TYPE: DNA
<213> ORGANISM: Artificial Sequence
<220> FEATURE:
<223> OTHER INFORMATION: cDNA

<400> SEQUENCE: 6
gacattgtgc tgacccaatc tccatcttat cttgctgcat ctcctggaga aaccattact      60
attaattgca gggcaagtaa gagcattagc aaatatttag cctggtatca agagagacct     120
gggaaaaaat aaacttctta tctattctgg atccactttg caatctggaa ttccatcaag     180
gttcagtggc agtggatctg gtacagattt cactctcacc atcagtagcc tggagcctga     240
agattttgca atgatactgt caacagcata tgaatatcc gttcacgttc ggtgctggga     300
ccaagctgga gctgaaa                                                     317

<210> SEQ ID NO 7
<211> LENGTH: 356
<212> TYPE: DNA
<213> ORGANISM: Artificial Sequence
<220> FEATURE:
<223> OTHER INFORMATION: cDNA

<400> SEQUENCE: 7
gaggtgcagc tgcagcagtc aggacctgag ctggtgaagc ctggggcttc agtgaagttg      60
tcctgcaaga cttctggcta caccttcaca agctacgata tgaactgggt gaaacagagg     120
cctggacgga cttgagtgga ttggttggat ttttcctaga gatggtagta ctaagttcaa     180
tgagaagttc aagggcaagg ccacattgac tgtagacaca tcctccacca cagcgtacat     240
ggaactccac agctacatct gaggactctg cggtctattt ctgtgcaaga gcggagatct     300
tctttgatta cggctttgac tactggggcc aaggcaccac tctcacagtc tcctca        356

<210> SEQ ID NO 8
<211> LENGTH: 365
<212> TYPE: DNA
<213> ORGANISM: Artificial Sequence
<220> FEATURE:
<223> OTHER INFORMATION: cDNA

<400> SEQUENCE: 8
gaggtgaagg tggtggaatc tggaggaggc ttggtacagc ctggggttc tctgagactc       60 tcctgtgcaa cttctgggtt caccttcagt gatttctaca tggagtgggt ccgccagcct     120
ccagggaaga ctggagtgga ttgctgcaag tagaaacaaa gctaatgatt atacaacaga     180
gtacagtgca tctgtgaagg gtcggttcat cgtctccaga gacacttccc aaagcatcct     240
```

```
ctaccttcag ctgaatgccc tgagagctga ggacactgcc atttattact gtgcaagaaa    300
ttactacgat agtagctact ggtacttcga tgtctggggc gcagggacca cggtcagtct    360
cctca                                                                365
```

<210> SEQ ID NO 9
<211> LENGTH: 134
<212> TYPE: PRT
<213> ORGANISM: Artificial Sequence
<220> FEATURE:
<223> OTHER INFORMATION: antibody fragment

<400> SEQUENCE: 9

```
Leu Pro Glu Val Gln Leu Glu Glu Ser Gly Ala Asp Leu Val Lys Pro
1               5                   10                  15

Gly Thr Ser Val Lys Leu Ser Cys Lys Ala Ser Gly Phe Thr Phe Thr
            20                  25                  30

Ser Tyr Trp Met His Trp Val Lys Gln Arg Pro Gly Gln Gly Leu Glu
        35                  40                  45

Trp Ile Gly Val Ile His Pro Asn Ser Gly Asn Thr Lys Tyr Asn Glu
    50                  55                  60

Lys Phe Arg Ser Glu Ala Thr Leu Thr Val Asp Lys Ser Ser Asn Thr
65                  70                  75                  80

Ala Tyr Ile Gln Leu Ser Ser Leu Thr Ser Glu Asp Ser Ala Val Tyr
                85                  90                  95

Tyr Cys Ala Arg Glu Met Trp Asn Tyr Gly Asn Ser Trp Tyr Phe Asp
            100                 105                 110

Val Trp Gly Thr Gly Thr Thr Val Thr Val Ser Ser Ala Lys Thr Thr
        115                 120                 125

Pro Pro Ser Val Tyr Ser
    130
```

<210> SEQ ID NO 10
<211> LENGTH: 134
<212> TYPE: PRT
<213> ORGANISM: Artificial Sequence
<220> FEATURE:
<223> OTHER INFORMATION: antibody fragment of heavy chain

<400> SEQUENCE: 10

```
Leu Pro Gln Val Lys Leu Glu Glu Ser Gly Ala Asp Leu Val Lys Pro
1               5                   10                  15

Gly Thr Ser Val Lys Leu Ser Cys Lys Ala Ser Gly Phe Thr Phe Thr
            20                  25                  30

Ser Tyr Trp Met His Trp Val Lys Gln Arg Pro Gly Gln Gly Leu Glu
        35                  40                  45

Trp Ile Gly Val Ile His Pro Asn Ser Gly Asn Thr Lys Tyr Asn Glu
    50                  55                  60

Lys Phe Arg Ser Glu Ala Thr Leu Thr Val Asp Lys Ser Ser Asn Thr
65                  70                  75                  80

Ala Tyr Ile Gln Leu Ser Ser Leu Thr Ser Glu Asp Ser Ala Val Tyr
                85                  90                  95

Tyr Cys Ala Arg Glu Met Trp Asn Tyr Gly Asn Ser Trp Tyr Phe Asp
            100                 105                 110

Val Trp Gly Thr Gly Thr Thr Val Thr Val Ser Ser Ala Lys Thr Thr
        115                 120                 125

Pro Pro Ser Val Tyr Ser
    130
```

<210> SEQ ID NO 11
<211> LENGTH: 134
<212> TYPE: PRT
<213> ORGANISM: Artificial Sequence
<220> FEATURE:
<223> OTHER INFORMATION: antibody fragment of heavy chain

<400> SEQUENCE: 11

Leu Pro Glu Val Gln Leu Glu Glu Ser Gly Ala Asp Leu Val Lys Pro
1               5                   10                  15

Gly Thr Ser Val Lys Leu Ser Cys Lys Ala Ser Gly Phe Thr Phe Thr
            20                  25                  30

Ser Tyr Trp Met His Trp Val Lys Gln Arg Pro Gly Gln Gly Leu Glu
        35                  40                  45

Trp Ile Gly Val Ile His Pro Asn Ser Gly Asn Thr Lys Tyr Asn Glu
    50                  55                  60

Lys Phe Arg Ser Glu Ala Thr Leu Thr Val Asp Lys Ser Ser Asn Thr
65                  70                  75                  80

Ala Tyr Ile Gln Leu Ser Ser Leu Thr Ser Glu Asp Ser Ala Val Tyr
                85                  90                  95

Tyr Cys Ala Arg Glu Met Trp Asn Tyr Gly Asn Ser Trp Tyr Phe Asp
            100                 105                 110

Val Trp Gly Thr Gly Thr Thr Val Thr Val Ser Ser Ala Lys Thr Thr
        115                 120                 125

Pro Pro Ser Val Tyr Ser
        130

<210> SEQ ID NO 12
<211> LENGTH: 118
<212> TYPE: PRT
<213> ORGANISM: Artificial Sequence
<220> FEATURE:
<223> OTHER INFORMATION: antibody light chain variable region

<400> SEQUENCE: 12

Asp Ile Val Leu Thr Gln Thr Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Pro Ser Trp Lys Asn Gly Leu Met
            100                 105                 110

Leu His Gln Leu Tyr Pro
        115

<210> SEQ ID NO 13
<211> LENGTH: 118
<212> TYPE: PRT
<213> ORGANISM: Artificial Sequence
<220> FEATURE:
<223> OTHER INFORMATION: antibody light chain variable region

<400> SEQUENCE: 13

Asp Ile Val Leu Thr Gln Thr Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Pro Ser Trp Lys Asn Gly Leu Met
            100                 105                 110

Leu His Gln Leu Tyr Pro
        115

<210> SEQ ID NO 14
<211> LENGTH: 118
<212> TYPE: PRT
<213> ORGANISM: Artificial Sequence
<220> FEATURE:
<223> OTHER INFORMATION: antibody light chain variable region

<400> SEQUENCE: 14

Asp Ile Val Ile Thr Gln Thr Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Pro Ser Trp Lys Asn Gly Leu Met
            100                 105                 110

Leu His Gln Leu Tyr Pro
        115

<210> SEQ ID NO 15
<211> LENGTH: 402
<212> TYPE: DNA
<213> ORGANISM: Artificial Sequence
<220> FEATURE:
<223> OTHER INFORMATION: cDNA

<400> SEQUENCE: 15
cttccggagg tacagctgga ggagtcaggg gctgacctgg taaagcctgg gacttcagtg      60
aaattgtcct gcaaggcttc tggcttcact ttcaccagct actggatgca ctgggtgaag     120
cagaggcctg acaaggcct tgagtggatt ggagtgattc atcctaacag tggtaatact      180
aagtacaatg aaaaattcag gagtgaggcc acactgacag tagacaagtc ctccaacaca     240

```
gcctacatac aactcagcag cctgacatct gaggactctg cggtctatta ctgtgcaaga    300
gagatgtgga actacggtaa tagctggtat ttcgatgtct ggggcacagg gaccacggtc    360
accgtctcct cagccaaaac gacacccca tctgtctatt cc                       402
```

<210> SEQ ID NO 16
<211> LENGTH: 402
<212> TYPE: DNA
<213> ORGANISM: Artificial Sequence
<220> FEATURE:
<223> OTHER INFORMATION: cDNA

<400> SEQUENCE: 16

```
cttccgcaag tcaagctgga ggagtcaggg gctgacctgg taaagcctgg gacttcagtg     60
aaattgtcct gcaaggcttc tggcttcact ttcaccagct actggatgca ctgggtgaag    120
cagaggcctg gacaaggcct tgagtggatt ggagtgattc atcctaacag tggtaatact    180
aagtacaatg aaaaattcag gagtgaggcc acactgacag tagacaagtc ctccaacaca    240
gcctacatac aactcagcag cctgacatct gaggactctg cggtctatta ctgtgcaaga    300
gagatgtgga actacggtaa tagctggtat ttcgatgtct ggggcacagg gaccacggtc    360
accgtctcct cagccaaaac gacaccccca tctgtctatt cc                       402
```

<210> SEQ ID NO 17
<211> LENGTH: 402
<212> TYPE: DNA
<213> ORGANISM: Artificial Sequence
<220> FEATURE:
<223> OTHER INFORMATION: cDNA

<400> SEQUENCE: 17

```
cttccggaag tacagctgga ggagtcaggg gctgacctgg taaagcctgg gacttcagtg     60
aaattgtcct gcaaggcttc tggcttcact ttcaccagct actggatgca ctgggtgaag    120
cagaggcctg gacaaggcct tgagtggatt ggagtgattc atcctaacag tggtaatact    180
aagtacaatg aaaaattcag gagtgaggcc acactgacag tagacaagtc ctccaacaca    240
gcctacatac aactcagcag cctgacatct gaggactctg cggtctatta ctgtgcaaga    300
gagatgtgga actacggtaa tagctggtat ttcgatgtct ggggcacagg gaccacggtc    360
accgtctcct cagccaaaac gacaccccca tctgtctatt cc                       402
```

<210> SEQ ID NO 18
<211> LENGTH: 402
<212> TYPE: DNA
<213> ORGANISM: Artificial Sequence
<220> FEATURE:
<223> OTHER INFORMATION: cDNA

<400> SEQUENCE: 18

```
cttccggagg tacagctgga ggagtcaggg gctgacctgg taaagcctgg gacttcagtg     60
aaattgtcct gcaaggcttc tggcttcact ttcaccagct actggatgca ctgggtgaag    120
cagaggcctg gacaaggcct tgagtggatt ggagtgattc atcctaacag tggtaatact    180
aagtacaatg aaaaattcag gagtgaggcc acactgacag tagacaagtc ctccaacaca    240
gcctacatac aactcagcag cctgacatct gaggactctg cggtctatta ctgtgcaaga    300
gagatgtgga actacggtaa tagctggtat ttcgatgtct ggggcacagg gaccacggtc    360
accgtctcct cagccaaaac gacaccccca tctgtctatt cc                       402
```

<210> SEQ ID NO 19
<211> LENGTH: 402
<212> TYPE: DNA
<213> ORGANISM: Artificial Sequence
<220> FEATURE:
<223> OTHER INFORMATION: cDNA

<400> SEQUENCE: 19

```
cttccgcaag tcaagctgga ggagtcaggg gctgacctgg taaagcctgg gacttcagtg      60
aaattgtcct gcaaggcttc tggcttcact ttcaccagct actggatgca ctgggtgaag    120
cagaggcctg gacaaggcct tgagtggatt ggagtgattc atcctaacag tggtaatact    180
aagtacaatg aaaaattcag gagtgaggcc acactgacag tagacaagtc ctccaacaca    240
gcctacatac aactcagcag cctgacatct gaggactctg cggtctatta ctgtgcaaga    300
gagatgtgga actacggtaa tagctggtat ttcgatgtct ggggcacagg gaccacggtc    360
accgtctcct cagccaaaac gacacccccca tctgtctatt cc                       402
```

<210> SEQ ID NO 20
<211> LENGTH: 402
<212> TYPE: DNA
<213> ORGANISM: Artificial Sequence
<220> FEATURE:
<223> OTHER INFORMATION: cDNA

<400> SEQUENCE: 20

```
cttccggaag tacagctgga ggagtcaggg gctgacctgg taaagcctgg gacttcagtg      60
aaattgtcct gcaaggcttc tggcttcact ttcaccagct actggatgca ctgggtgaag    120
cagaggcctg gacaaggcct tgagtggatt ggagtgattc atcctaacag tggtaatact    180
aagtacaatg aaaaattcag gagtgaggcc acactgacag tagacaagtc ctccaacaca    240
gcctacatac aactcagcag cctgacatct gaggactctg cggtctatta ctgtgcaaga    300
gagatgtgga actacggtaa tagctggtat ttcgatgtct ggggcacagg gaccacggtc    360
accgtctcct cagccaaaac gacacccccca tctgtctatt cc                       402
```

<210> SEQ ID NO 21
<211> LENGTH: 127
<212> TYPE: PRT
<213> ORGANISM: Artificial Sequence
<220> FEATURE:
<223> OTHER INFORMATION: antibody fragment of heavy chain

<400> SEQUENCE: 21

Leu Pro Glu Val Gln Leu Glu Glu Ser Gly Pro Gly Leu Val Ala Pro
1               5                   10                  15

Ser Gln Ser Leu Ser Ile Thr Cys Thr Val Ser Gly Phe Ser Leu Thr
            20                  25                  30

Arg Tyr Gly Val His Trp Val Arg Gln Pro Pro Gly Lys Gly Leu Glu
        35                  40                  45

Trp Leu Gly Val Ile Trp Thr Ala Gly Asn Thr Asn Tyr Asn Ser Ala
    50                  55                  60

Leu Met Ser Arg Leu Ser Ile Ser Lys Asp Asn Ser Lys Thr Gln Val
65                  70                  75                  80

Phe Leu Lys Met Asn Ser Leu Gln Thr Asp Asp Thr Ala Met Tyr Tyr
                85                  90                  95

Cys Ala Arg Asp Asp Pro Ser Met Ala Tyr Trp Gly Gln Gly Thr Ser
            100                 105                 110

Val Thr Val Ser Ser Ala Lys Thr Thr Pro Pro Ser Val Tyr Ser

-continued

```
                115                 120                 125
```

<210> SEQ ID NO 22
<211> LENGTH: 127
<212> TYPE: PRT
<213> ORGANISM: Artificial Sequence
<220> FEATURE:
<223> OTHER INFORMATION: antibody fragment of heavy chain

<400> SEQUENCE: 22

```
Leu Pro Gln Val Gln Leu Glu Gln Ser Gly Pro Gly Leu Val Ala Pro
1               5                   10                  15

Ser Gln Ser Leu Ser Ile Thr Cys Thr Val Ser Gly Phe Ser Leu Thr
            20                  25                  30

Arg Tyr Gly Val His Trp Val Arg Gln Pro Pro Gly Lys Gly Leu Glu
        35                  40                  45

Trp Leu Gly Val Ile Trp Thr Ala Gly Asn Thr Asn Tyr Asn Ser Ala
    50                  55                  60

Leu Met Ser Arg Leu Ser Ile Ser Lys Asp Asn Ser Lys Thr Gln Val
65                  70                  75                  80

Phe Leu Lys Met Asn Ser Leu Gln Thr Asp Asp Thr Ala Met Tyr Tyr
                85                  90                  95

Cys Ala Arg Asp Asp Pro Ser Met Ala Tyr Trp Gly Gln Gly Thr Ser
            100                 105                 110

Val Thr Val Ser Ser Ala Lys Thr Thr Pro Pro Ser Val Tyr Ser
        115                 120                 125
```

<210> SEQ ID NO 23
<211> LENGTH: 127
<212> TYPE: PRT
<213> ORGANISM: Artificial Sequence
<220> FEATURE:
<223> OTHER INFORMATION: antibody fragment of heavy chain

<400> SEQUENCE: 23

```
Leu Pro Gln Val Lys Leu Gln Gln Ser Gly Pro Gly Leu Val Ala Pro
1               5                   10                  15

Ser Gln Ser Leu Ser Ile Thr Cys Thr Val Ser Gly Phe Ser Leu Thr
            20                  25                  30

Arg Tyr Gly Val His Trp Val Arg Gln Pro Pro Gly Lys Gly Leu Glu
        35                  40                  45

Trp Leu Gly Val Ile Trp Thr Ala Gly Asn Thr Asn Tyr Asn Ser Ala
    50                  55                  60

Leu Met Ser Arg Leu Ser Ile Ser Lys Asp Asn Ser Lys Thr Gln Val
65                  70                  75                  80

Phe Leu Lys Met Asn Ser Leu Gln Thr Asp Asp Thr Ala Met Tyr Tyr
                85                  90                  95

Cys Ala Arg Asp Asp Pro Ser Met Ala Tyr Trp Gly Gln Gly Thr Ser
            100                 105                 110

Val Thr Val Ser Ser Ala Lys Thr Thr Pro Pro Ser Val Tyr Ser
        115                 120                 125
```

<210> SEQ ID NO 24
<211> LENGTH: 116
<212> TYPE: PRT
<213> ORGANISM: Artificial Sequence
<220> FEATURE:
<223> OTHER INFORMATION: antibody light chain variable region

<400> SEQUENCE: 24

```
Asp Ile Val Leu Thr Gln Thr Pro Ala Ile Met Ser Val Ser Pro Gly
1               5                   10                  15

Glu Lys Val Thr Ile Thr Cys Ser Ala Ser Ser Ser Val Ser Tyr Met
                20                  25                  30

His Trp Phe Gln Gln Lys Pro Gly Thr Ser Pro Lys Leu Trp Ile Tyr
            35                  40                  45

Ser Thr Ser Asn Leu Ala Ser Gly Val Pro Ala Arg Phe Ser Gly Ser
        50                  55                  60

Gly Ser Gly Thr Ser Tyr Ser Leu Thr Ile Ser Arg Thr Glu Ala Glu
65                  70                  75                  80

Asp Ala Ala Thr Tyr Tyr Cys Gln Gln Arg Ser Ser Tyr Pro Tyr Thr
                85                  90                  95

Phe Gly Gly Gly Thr Lys Leu Glu Ile Lys Arg Ala Asp Ala Ala Pro
            100                 105                 110

Thr Val Ser Thr
        115

<210> SEQ ID NO 25
<211> LENGTH: 116
<212> TYPE: PRT
<213> ORGANISM: Artificial Sequence
<220> FEATURE:
<223> OTHER INFORMATION: antibody light chain variable region

<400> SEQUENCE: 25

Asp Ile Val Leu Thr Gln Thr Pro Ala Ile Met Ser Val Ser Pro Gly
1               5                   10                  15

Glu Lys Val Thr Ile Thr Cys Ser Ala Ser Ser Ser Val Ser Tyr Met
                20                  25                  30

His Trp Phe Gln Gln Lys Pro Gly Thr Ser Pro Lys Leu Trp Ile Tyr
            35                  40                  45

Ser Thr Ser Asn Leu Ala Ser Gly Val Pro Ala Arg Phe Ser Gly Ser
        50                  55                  60

Gly Ser Gly Thr Ser Tyr Ser Leu Thr Ile Ser Arg Thr Glu Ala Glu
65                  70                  75                  80

Asp Ala Ala Thr Tyr Tyr Cys Gln Gln Arg Ser Ser Tyr Pro Tyr Thr
                85                  90                  95

Phe Gly Gly Gly Thr Lys Leu Glu Ile Lys Arg Ala Asp Ala Ala Pro
            100                 105                 110

Thr Val Ser Thr
        115

<210> SEQ ID NO 26
<211> LENGTH: 116
<212> TYPE: PRT
<213> ORGANISM: Artificial Sequence
<220> FEATURE:
<223> OTHER INFORMATION: antibody light chain variable region

<400> SEQUENCE: 26

Asp Ile Val Leu Thr Gln Thr Pro Ala Ile Met Ser Val Ser Pro Gly
1               5                   10                  15

Glu Lys Val Thr Ile Thr Cys Ser Ala Ser Ser Ser Val Ser Tyr Met
                20                  25                  30

His Trp Phe Gln Gln Lys Pro Gly Thr Ser Pro Lys Leu Trp Ile Tyr
            35                  40                  45

Ser Thr Ser Asn Leu Ala Ser Gly Val Pro Ala Arg Phe Ser Gly Ser
```

```
                50                  55                  60
Gly Ser Gly Thr Ser Tyr Ser Leu Thr Ile Ser Arg Thr Glu Ala Glu
 65                  70                  75                  80

Asp Ala Ala Thr Tyr Tyr Cys Gln Gln Arg Ser Ser Tyr Pro Tyr Thr
                 85                  90                  95

Phe Gly Gly Gly Thr Lys Leu Glu Ile Lys Arg Ala Asp Ala Ala Pro
            100                 105                 110

Thr Val Ser Thr
        115

<210> SEQ ID NO 27
<211> LENGTH: 381
<212> TYPE: DNA
<213> ORGANISM: Artificial Sequence
<220> FEATURE:
<223> OTHER INFORMATION: cDNA

<400> SEQUENCE: 27
cttccggagg tgcagctgga ggagtcagga cctggcctgg tggcgccctc acagagcctg      60
tccatcactt gcactgtctc tggattttca ttaaccagat atggtgtaca ctgggttcgc     120
cagcctccag gaaagggtct ggagtggctg ggagtaatct ggactgctgg aaacacaaat    180
tataattcgg ctctcatgtc cagactgagc atcagcaaag acaactccaa gacccaagtt    240
ttcttaaaaa tgaacagtct ccaaactgat gacacagcca tgtactactg tgccagagat    300
gatccctcta tggcctactg gggtcaagga acctcagtca ccgtctcctc agccaaaacg    360 acaccccat ctgtctattc c                                              381

<210> SEQ ID NO 28
<211> LENGTH: 381
<212> TYPE: DNA
<213> ORGANISM: Artificial Sequence
<220> FEATURE:
<223> OTHER INFORMATION: cDNA

<400> SEQUENCE: 28
cttccgcaag tacagctgga gcagtcagga cctggcctgg tggcgccctc acagagcctg     60
tccatcactt gcactgtctc tggattttca ttaaccagat atggtgtaca ctgggttcgc    120
cagcctccag gaaagggtct ggagtggctg ggagtaatct ggactgctgg aaacacaaat    180
tataattcgg ctctcatgtc cagactgagc atcagcaaag acaactccaa gacccaagtt    240
ttcttaaaaa tgaacagtct ccaaactgat gacacagcca tgtactactg tgccagagat    300
gatccctcta tggcctactg gggtcaagga acctcagtca ccgtctcctc agccaaaacg    360 acaccccat ctgtctattc c                                              381

<210> SEQ ID NO 29
<211> LENGTH: 381
<212> TYPE: DNA
<213> ORGANISM: Artificial Sequence
<220> FEATURE:
<223> OTHER INFORMATION: cDNA

<400> SEQUENCE: 29
cttccgcagg taaagctgca gcagtctgga cctggcctgg tggcgccctc acagagcctg    60
tccatcactt gcactgtctc tggattttca ttaaccagat atggtgtaca ctgggttcgc   120
cagcctccag gaaagggtct ggagtggctg ggagtaatct ggactgctgg aaacacaaat   180
tataattcgg ctctcatgtc cagactgagc atcagcaaag acaactccaa gacccaagtt   240
```

```
ttcttaaaaa tgaacagtct ccaaactgat gacacagcca tgtactactg tgccagagat      300
gatccctcta tggcctactg gggtcaagga acctcagtca ccgtctcctc agccaaaacg      360 acaccccat ctgtctattc c                                                 381

<210> SEQ ID NO 30
<211> LENGTH: 350
<212> TYPE: DNA
<213> ORGANISM: Artificial Sequence
<220> FEATURE:
<223> OTHER INFORMATION: cDNA

<400> SEQUENCE: 30
gggacattgt gctgacccaa actccagcaa tcatgtctgt atctccaggg gagaaggtca       60
ccataacctg tagtgccagc tcaagtgtaa gttacatgca ctggttccag cagaagccag      120
gcacttctcc caaactctgg atttatagca catccaacct ggcttctgga gtccctgctc      180
gcttcagtgg cagtggatct gggacctctt actctctcac aatcagccga acggaggctg      240
aagatgctgc cacttattac tgccaacaaa ggagtagtta cccgtacacg ttcggagggg      300
ggaccaagct ggaaataaaa cgggctgatg ctgcaccaac tgtatccacc                 350

<210> SEQ ID NO 31
<211> LENGTH: 350
<212> TYPE: DNA
<213> ORGANISM: Artificial Sequence
<220> FEATURE:
<223> OTHER INFORMATION: cDNA

<400> SEQUENCE: 31
gggatattgt gctcacacaa actccagcaa tcatgtctgt atctccaggg gagaaggtca       60
ccataacctg tagtgccagc tcaagtgtaa gttacatgca ctggttccag cagaagccag      120
gcacttctcc caaactctgg atttatagca catccaacct ggcttctgga gtccctgctc      180
gcttcagtgg cagtggatct gggacctctt actctctcac aatcagccga acggaggctg      240
aagatgctgc cacttattac tgccaacaaa ggagtagtta cccgtacacg ttcggagggg      300
ggaccaagct ggaaataaaa cgggctgatg ctgcaccaac tgtatccacc                 350

<210> SEQ ID NO 32
<211> LENGTH: 350
<212> TYPE: DNA
<213> ORGANISM: Artificial Sequence
<220> FEATURE:
<223> OTHER INFORMATION: cDNA

<400> SEQUENCE: 32
gggacattgt gctcacacag actccagcaa tcatgtctgt atctccaggg gagaaggtca       60
ccataacctg tagtgccagc tcaagtgtaa gttacatgca ctggttccag cagaagccag      120
gcacttctcc caaactctgg atttatagca catccaacct ggcttctgga gtccctgctc      180
gcttcagtgg cagtggatct gggacctctt actctctcac aatcagccga acggaggctg      240
aagatgctgc cacttattac tgccaacaaa ggagtagtta cccgtacacg ttcggagggg      300
ggaccaagct ggaaataaaa cgggctgatg ctgcaccaac tgtatccacc                 350
```